United States Patent [19]

Nakajima et al.

[11] Patent Number: 4,905,652

[45] Date of Patent: Mar. 6, 1990

[54] DEVICE FOR MEASURING A COMPONENT OF A GASEOUS MIXTURE

[75] Inventors: Toyohei Nakajima; Yasushi Okada; Toshiyuki Mieno; Nobuyuki Ohno, all of Saitama, Japan

[73] Assignee: Honda Giken Kogyo Kabushiki Kaisha, Tokyo, Japan

[21] Appl. No.: 361,717

[22] Filed: May 30, 1989

Related U.S. Application Data

[63] Continuation of Ser. No. 249,265, Sep. 23, 1988, abandoned, which is a continuation of Ser. No. 919,237, Oct. 14, 1986, abandoned.

[30] Foreign Application Priority Data

| Oct. 18, 1985 | [JP] | Japan | 60-232888 |
| Nov. 2, 1985 | [JP] | Japan | 60-246847 |
| Nov. 2, 1985 | [JP] | Japan | 60-246844 |
| Nov. 2, 1985 | [JP] | Japan | 60-246845 |
| Nov. 2, 1985 | [JP] | Japan | 60-246846 |
| Nov. 25, 1985 | [JP] | Japan | 60-265353 |
| Nov. 25, 1985 | [JP] | Japan | 60-265355 |
| Nov. 25, 1985 | [JP] | Japan | 60-265354 |

[51] Int. Cl.⁴ .................... G01N 27/58; F02D 41/22
[52] U.S. Cl. ................... 123/479; 123/489; 204/401; 204/410; 204/412; 204/425
[58] Field of Search ............ 123/479, 440, 489; 204/412, 15, 401, 410, 425, 426; 60/276; 73/1 G, 23; 338/34

[56] References Cited

U.S. PATENT DOCUMENTS

| 4,121,548 | 10/1978 | Hattori et al. | 123/33 EE |
| 4,158,166 | 6/1979 | Isenberg | 324/29 |
| 4,272,329 | 6/1981 | Hetrick | 204/1 T |
| 4,272,331 | 6/1981 | Hetrick | 204/1 T |
| 4,285,790 | 8/1981 | Isenberg | 204/410 |
| 4,547,281 | 10/1985 | Wang et al. | 204/424 |
| 4,568,443 | 2/1986 | Asayama et al. | 204/410 |

FOREIGN PATENT DOCUMENTS

| 52-72286 | 6/1977 | Japan | 204/425 |
| 59-192955 | 11/1984 | Japan | 204/425 |
| 1523550 | 9/1978 | United Kingdom | 204/425 |

OTHER PUBLICATIONS

SAE Technical Paper Series (841250), "Extended Range Air-to-Fuel Ratio Sensor", (1984).
SAE Technical Paper Series (850378), "Multi-Layered Zirconia Oxygen Sensor for Lean Burn Engine Application", (1985).
SAE Technical Paper Series (850380), "Lean Mixture Sensor", (1985).

*Primary Examiner*—Tony M. Argenbright
*Attorney, Agent, or Firm*—Lyon & Lyon

[57] ABSTRACT

A device for detecting and measuring the concentration of a gas in a mixture of gas such as oxygen in the exhaust gas of an internal combustion engine and circuits for using that measurement to control the air-fuel ratio supplied to the engine. The detecting device has two separate gas residence chamber with different diffusion resistance openings for each chamber and separate pairs of electrodes for each chamber whereby the measurement can be separately made in each chamber. The particular chamber selected for measurement may be done on the basis of whether the air-fuel ratio is lean or rich whereby a substantially linear reading results for all ratios or on the basis of the transition-state or steady-state operating condition of the engine to provide either more rapid or more accurate readings. Further, by using the cells from both chambers to compare their readings and standards, the actual readings can be corrected for abnormalties that may occur after a period of use or to indicate the detector has become defective.

48 Claims, 12 Drawing Sheets

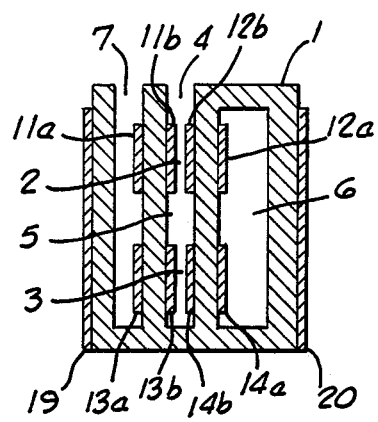
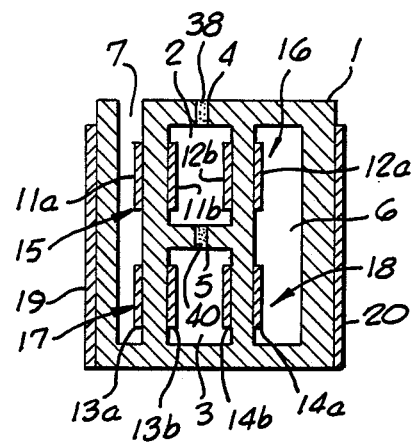
FIG. 13.  FIG. 14.
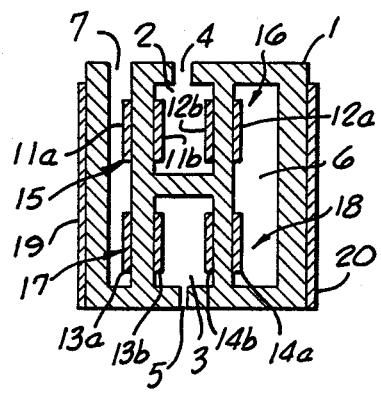
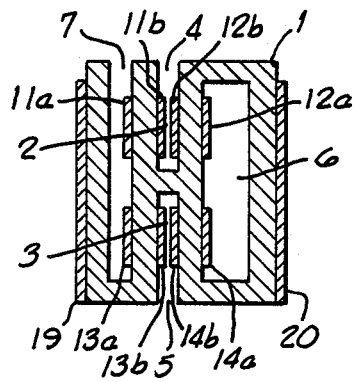
FIG. 15.  FIG. 16.

DEVICE FOR MEASURING A COMPONENT OF A GASEOUS MIXTURE

This application is a continuation, of application Ser. No. 249,265, filed 9/12/88, now abandoned, which is a continuation of Ser. No. 919,237, filed 10/14/86, now abandoned.

This invention relates to a device, for detecting the proportion of one or more specific gases in a mixture of gases and, in particular, relates to such a device for use in detecting the concentration of oxygen in the exhaust gas from an internal combustion engine in an automobile although the device is useable for numerous other purposes, such as monitoring the oxygen content in the air mine shafts or an undesirable gas in the gases discharged from an industrial process. However, since the principle use of this device presently contemplated by the inventors is an oxygen concentration sensor for the exhaust of an automobile engine for in turn controlling the air-fuel ratio of the intake air mixture supplied to the combustion chambers of the engine, the description herein will relate to that use.

It is now well known to provide an automobile engine with an air-fuel (hereinafter "A/F") ratio control apparatus with an oxygen concentration sensor for detecting the concentration of oxygen in the engine exhaust gas and a feedback control device for attempting to control the A/F ratio of gas mixture to be supplied to the internal combustion engine to a target A/F ratio according to the result of the oxygen concentration detection for the purpose of minimizing the objectionable gases in the exhaust gas from the engine and for reducing the fuel consumption. There are conventional oxygen concentration detectors employed in A/F ratio control devices designed to generate an output proportional to the concentration of oxygen in the measured gas, as disclosed in Japanese Patent Laid-Open No. 52-72286 and a similar British Pat. No. 1,523,550. In those two patents a threshold current type oxygen concentration detector is disclosed that includes a pair of electrodes provided on both surfaces of a plate-like oxygen ion conductive solid electrolyte member and a gas residence chamber formed by a part of one electrode surface of the solid electrolyte member which chamber is communicated through an induction hole to the measured gas. In the conventional oxygen concentration detector, the oxygen ion conductive solid electrolyte member and the pair of electrodes function as an oxygen pump element. When the electrode on the gas residence chamber side is defined as a negative pole, and current is supplied to both the electrodes, oxygen gas in the gas residence chamber is ionized at the negative pole to move through the solid electrolyte member to the positive pole, where oxygen gas is discharged. The value of threshold current capable of flowing between both the electrodes is almost constant irrespective of voltage applied, and is proportional to the concentration of oxygen in the measured gas. Therefore, the concentration of oxygen in the measured gas may be measured by detecting the value of the threshold current. However, in controlling the A/F ratio by use of the oxygen concentration detector as above mentioned, it is impossible to obtain an output proportion to the concentration of oxygen in the exhaust gas in an A/F ratio region except a lean region where the A/F ratio of mixture gas is leaner than the theoretical target A/F ratio. Therefore, in the case that a target A/F ratio is set in a rich region, the A/F ratio control cannot be performed by that type of device.

Another sensor is shown in U.S. Pat. No. 4,158,166 that includes an oxygen concentration sensor cell and an oxygen pump cell but it is only effective in detecting oxygen concentration in the rich A/F ratio region.

There is disclosed in Japanese Patent Laid-Open No. 59-192955 and the corresponding U.S. Pat. No. 4,568,443 another type of oxygen concentration detector designed to obtain an output proportional to the concentration of oxygen in the exhaust gas in both lean and rich regions of the A/F ratio. That oxygen concentration detector includes two plate-like oxygen ion conductive solid electrolyte members, two pairs of electrodes mounted to the solid electrolyte members, a gas residence chamber formed by a part of one electrode surface of the solid electrolyte members which chamber is communicated through an induction hole to the measured gas, and an atmospheric chamber formed by the other electrode surface of one of the solid electrolyte members. In this conventional oxygen concentration detector, one of the oxygen ion conductive solid electrolyte members and one pair of electrodes function as an oxygen concentration ratio detecting cell element, while the other oxygen ion conductive solid electrolyte member and pair of electrodes function as an oxygen pump element. When voltage generated between the electrodes of the oxygen concentration ratio detecting cell element is greater than a reference voltage, current is supplied so as to permit oxygen ions to move in the oxygen pump element toward the electrode on the gas residence chamber side. In contrast, when the voltage generated between the electrodes of the oxygen concentration ratio detecting cell element is less than the reference voltage, current is supplied so as to permit the oxygen ions to move in the oxygen pump element toward the electrode on the opposite side as the gas residence chamber. Thus, the current value is proportional to the oxygen concentration in each of the two regions, that is the lean region and the rich region of the A/F ratio. However, in this conventional oxygen concentration detector, oxygen concentration detection characteristics in the rich region are different from those in the lean region, and it is impossible to obtain a detection output of oxygen concentration with good linearity in a wide region. Therefore, the detection output of oxygen concentration in the rich or lean region must be corrected which renders the A/F ratio control complicated.

Moreover, in the above oxygen concentration detector of the oxygen concentration proportional output type, oxygen concentration detection error is reduced as the induction hole becomes small, whereby the A/F ratio of the supplied mixture gas may be controlled with a high degree accuracy to thereby improve exhaust gas purification performance. Conversely, the oxygen concentration detection error increases as the induction hole becomes larger, although the speed of the response to a change in oxygen concentration is improved. Thus, there exists a conflict relationship between improving the oxygen concentration detection error and improving the response time of the sensor. However, it is also true that sometimes it is more important to obtain good drivability by rapidly controlling the A/F ratio of the supplied mixture gas according to a detection output of oxygen concentration having high response time rather than being extremely accurate in the exhaust gas purification performance of the engine. In other words, at such times, if merely the exhaust gas purification performance is improved, drivability is sacrificed just when it is most desired merely for the improvement in the purification performance.

Furthermore, with oxygen concentration detectors of the type described above that are located in the exhaust pipe of an internal combustion engine, it has been found that over a long period of time the effective size of the induction hole may be changed such as by the deposit of oxides and lead which reduces the effective size of the induction hole or by the deposited oxides breaking away with or without portions of the detector material forming the hole which abruptly increases the effective hole size. These occurrences greatly affect the output characteristics of the detector since the induction hole must be of a known and exact diameter and length for proper readings by the cell. Moreover, normally it is impossible to determine, as time passes, whether the effective size of the induction hole has changed whereby the absolute signals from the detector are in error, even though relative signals of changes remain essentially accurate.

Accordingly, it is an object of the present invention to provide a novel form of gas concentration detector for determining the proportion of a selected gas in a mixture of gases wherein (1) a substantially linear response can be obtained over a wide range of concentrations, (2) alternate cells are provided and can be selected for detecting concentration under different conditions, and/or (3) variations in response can be corrected for without correcting the cause of such variations.

A more detailed object of the present invention is to provide an oxygen concentration detector which may obtain a detection output of oxygen concentration in exhaust gases with good linearity over both lean and rich regions of the A/F ratio for an internal combustion engine.

Another object of the present invention is to provide an oxygen concentration detector which may be used to control the A/F ratio of an internal combustion engine by providing rapid detection during a changing state of operation of the engine for providing rapid control of the A/F ratio and by providing highly accurate but slower detection during steady-state engine operation for more precise A/F ratio control.

Still another object of this invention is to provide an oxygen concentration detector for an A/F ratio control for an internal combustion engine, which detector is located in the exhaust pipe and subject to accumulation of oxide deposits and other damaging conditions that affect the output signal and which detector has separate detection cells for periodically providing comparative signals and automatically correcting for response changes caused by the damaging conditions.

The oxygen concentration detector of the present invention comprises a base forming first and second gas residence chamber each having oxygen ion conductive solid electrolyte wall portions; a first two pairs of electrodes provided on the inside and outside surfaces of the electrolyte wall portions of said first gas residence chamber in such a manner that each electrode is arranged in opposed relation with respect to the electrolyte wall portions; a second two pairs of electrodes provided on the inside and outside surfaces of the electrolyte wall portions of said second gas residence chamber in such a manner that each electrode is arranged in opposed relation with respect to the electrolyte wall portions; a current supply means for supplying current to one of said first two pairs of electrodes according to the voltage differential between the voltage generated at the other of said first two pairs of electrodes and a first reference voltage, and also supplying current to one of said second two pairs of electrodes according to the voltage differential between the voltage generated at the other of said second two pairs of electrodes and a second reference voltage; a first gas diffusion restricting means for communicating said first gas residence chamber with the gas to be analyzed; and a second gas diffusion restricting means for communicating said second gas residence chamber with the gas to be analyzed and providing a different rate of diffusion than the first gas diffusion restricting means; whereby a detection value of oxygen concentration is obtained according to a current value supplied by said current supply means.

Other objects, features, advantages and details of the construction of the gas detector of this invention will be apparent from the following description of the preferred embodiments of this invention and the accompanying drawings wherein:

FIGS. 13, 14, 15, 16, 17, 18 and 19 are sectional views similar to FIG. 2 of alternative embodiments of the oxygen concentration detector of this invention.

Figure 1:
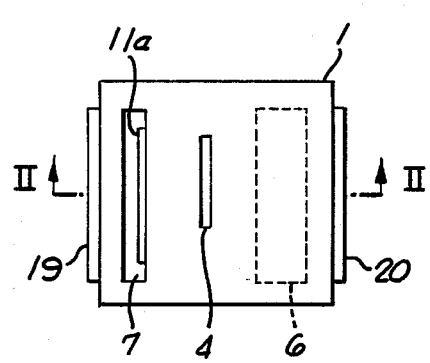
FIG. 1 is a plan view of the preferred embodiment of the oxygen or other gas detector of the present invention.
Figure 2:
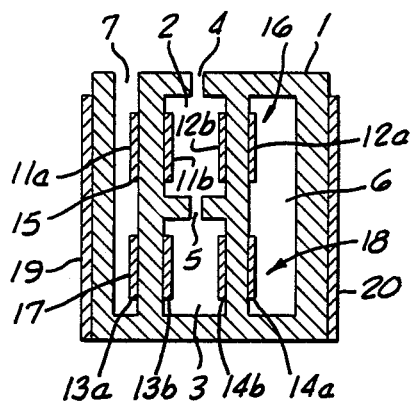
FIG. 2 is a sectional view of the gas detector taken substantially on the line 2—2 in FIG. 1.
Figure 3:
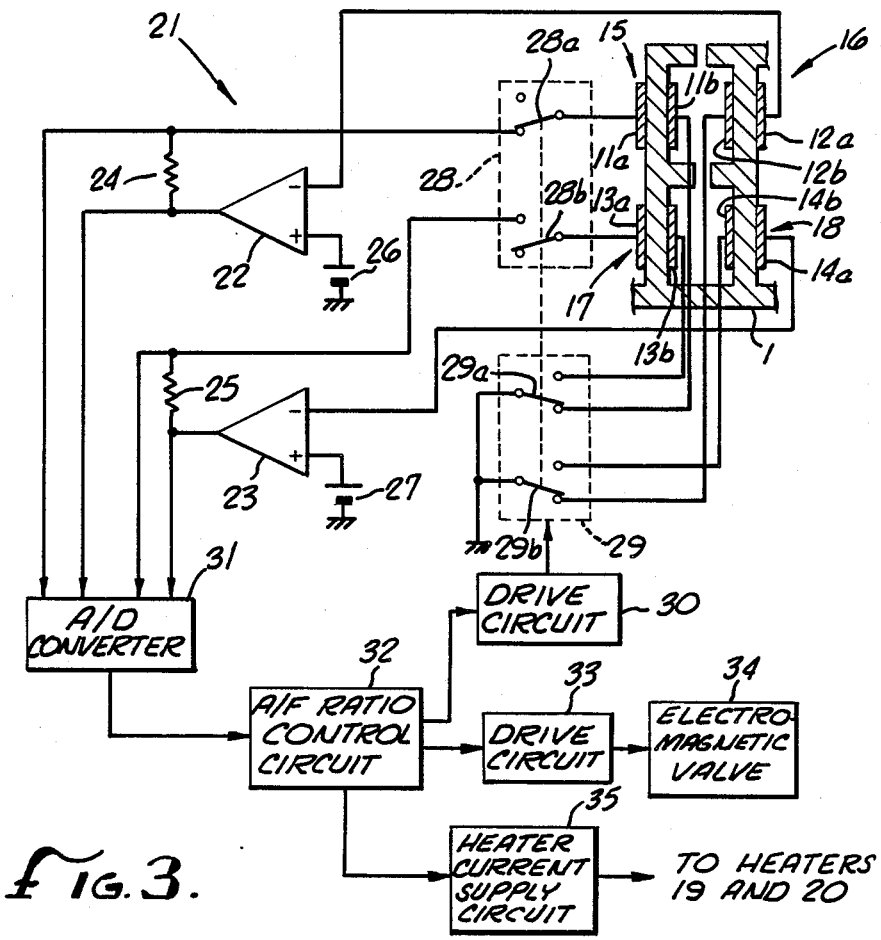
FIG. 3 is a circuit diagram of the A/F ratio control device using the oxygen detector of FIGS. 1 and 2.

Referring now to FIGS. 1, 2 and 3, the present invention will be described in connection with one useful application, namely an air-fuel ratio control system employing an oxygen concentration detector in the exhaust gas pipe of an internal combustion engine but it will be understood by those skilled in the art that the invention is also applicable to various other uses that require detection of the concentration or proportion of a selected gas or gases in a mixture of gases. In one form of the structure of the present invention there is provided a substantially cubic oxygen ion conductive solid electrolyte member 1. First and second gas residence chambers 2 and 3 are defined in the oxygen ion conductive solid electrolyte member 1. The first gas residence chamber 2 is provided with an induction hole 4 for the induction of an exhaust gas as a measured gas from the outside of the solid electrolyte member 1. The induction hole 4 is located in an exhaust pipe (not shown) of an internal combustion engine at a position where the exhaust gas may be easily induced into the first gas residence chamber 2. A communication hole 5 is formed through a wall portion between the first and second gas residence chambers 2 and 3, so that the exhaust gas may be induced from the induction hole 4 through the first gas residence chamber 2 and the communication hole 5 into the second gas residence chamber 3. A reference gas chamber 6 for receiving a reference gas, such as atmospheric air, is defined in the oxygen ion conductive solid electrolyte member 1 in such a manner as to be partitioned from the first and second gas residence chambers 1 and 2 by a wall portion. An electrode protection chamber 7 is defined in a wall portion of the electrolyte member 1 adjacent to but separated from the first and second gas residence chambers 2 and 3 on the opposite side as the reference gas chamber 6. A first pair of electrodes 11a and 11b are provided on a wall portion between the first gas residence chamber 2 and the electrode protection chamber 7, while a second pair of electrodes 12a and 12b are provided on a wall portion between the first gas residence chamber 2 and the reference gas chamber 6. Similarly, a third pair of electrodes 13a and 13b are provided on a wall portion between the second gas residence chamber 3 and the electrode protection chamber 7, while a fourth pair of electrodes 14a and 14b are provided on a wall portion between the second gas residence chamber 3 and the reference gas chamber 6.

Each pair of electrodes (12, 13, 14 and 15) and the solid electrolyte wall therebetween forms a separate electrochemical cell of a well known type that functions at very high temperatures, as described in the aforementioned patents. The function performed by each such cell in this invention will now be described. The solid electrolyte member 1 and the first pair of electrodes 11a and 11b act as a first oxygen pump element 15, while the solid electrolyte member 1 and the second pair of electrodes 12a and 12b act as a first cell element 16. Similarly, the solid electrolyte member 1 and the third pair of electrodes 13a and 13b act as a second oxygen pump element 17, while the solid electrolyte member 1 and the fourth pair of electrodes 14a and 14b act as a second cell element 18. Heater elements 19 and 20 are provided on respective outer wall surfaces of the electrodes protection chamber 7 and the reference gas chamber 6. The heater elements 19 and 20 are electrically connected with each other in parallel, and function to uniformly heat the first and second oxygen pump elements 15 and 17 as well as the first and second cell elements 16 and 18, and thereby improve the heat retaining property in the solid electrolyte member 1 and the performance of the cells in a known manner. The oxygen ion conductive solid electrolyte member 1 is integrally formed by a plurality of pieces. It is not necessary to form all of the wall portions of the first and second gas residence chambers of an oxygen ion conductive solid electrolyte, but at least that portion of each wall where the electrodes are provided must be formed of the solid electrolyte. The oxygen ion conductive solid electrolyte member 1 is preferably made of $ZrO_2$ (zirconium dioxide), and the electrodes 11a to 14b are made of Pt (platinum).

A current supply circuit 21 is connected to the first and second oxygen pump elements 15 and 17 as well as the first and second cell elements 16 and 18. As shown in FIG. 3, the current supply circuit 21 comprises differential amplifier circuits 22 and 23, current detection resistors 24 and 25, reference voltage sources 26 and 27 and selector circuits 28 and 29. The outside electrode 11a in electrode protection chamber 7 of the first oxygen pump element 15 is connected through a switch 28a in the selector circuit 28 and the current detection resistor 24 to an output terminal of the differential amplifier circuit 22, while the inside electrode 11b in the first gas residence chamber 2 is grounded through a switch 29a in the selector circuit 29. The outside electrode 12a in the reference gas chamber 6 of the first cell element 16 is connected to an inversion input terminal of the differential amplifier circuit 22, while the inside electrode 12b in the first gas residence chamber 2 is grounded through a switch 29b in the selector circuit 29. Similarly, the outside electrode 13a of the second oxygen pump element 17 is connected through a switch 28b in the selector circuit 28 and the current detection resistor 25 to an output terminal of the differential amplifier circuit 23, while the inside electrode 13b in the second gas residence chamber 3 is grounded through the switch 29a in the selector circuit 29. The outside electrode 14a of the second cell element 18 is connected to an inversion input terminal of the differential amplifier circuit 23, while the inside electrode 14b is grounded through the switch 29b in the selector circuit 29. The reference voltage source 26 is connected to a non-inversion input terminal of the differential amplifier circuit 22, while the reference voltage source 27 is connected to a non-inversion input terminal of the differential amplifier circuit 23. Output voltage of the reference voltage sources 26 and 27 is set at a voltage corresponding to a theoretical A/F ratio (0.4 V, for example). The output of a first sensor is developed across the current detection resistor 24, and the output of a second sensor is developed across the current detection resistor 25. The voltage differentials across the current detection resistors 24 and 25 are supplied separately through an A/D (Analog/Digital) converter 31 to an A/F ratio control circuit 32, and the pump current values $I_p(1)$ and $I_p(2)$ flowing in the current detection resistors 24 and 25 are read by the A/F ratio control circuit 32.

The A/F ratio control circuit 32 includes a microcomputer. A plurality of operation parameter detecting sensors (not shown) for detecting the engine rotational speed, absolute pressure in the intake suction pipe, coolant temperature, and other such parameters are connected to the A/F ratio control circuit 32, and an electromagnetic valve 34 is connected through a drive circuit 33 to the A/F ratio control circuit 32. The electromagnetic valve 34 is provided in a secondary air supply passage (not shown) that communicates with the intake manifold downstream of a throttle valve of the engine carburetor. The A/F ratio control circuit 32 acts to control a switch for selecting the operation of the selector circuits 28 and 29, and the drive circuit 30 acts to drive the selector circuits 28 and 29 according to a command from the A/F ratio control circuit 32. The differential amplifier circuits 22 and 23 are supplied with positive and negative supply voltage.

The heater elements 19 and 20 are supplied with current from a heater current supply circuit 35 to generate heat, thereby heating the oxygen pump elements 15 and 17 and the cell elements 16 and 18 to a suitable temperature higher than that of the exhaust gas for well known purposes.

In the aforementioned construction, the exhaust gas in the exhaust pipe is induced through the induction hole 4 into the first gas residence chamber 2, and is diffused therein. Further, the exhaust gas in the first gas residence chamber 2 is induced through the communication hole 5 into the second gas residence chamber 3, and is diffused therein.

Referring to FIG. 3, there is shown a selected condition of the first sensor wherein the selector circuits 28 and 29 are positioned such that the switch 28a connects the electrode 11a with the current detection resistor 24, and the switch 28b opens the connection line from the electrode 13a. Further, the switch 29a grounds the electrode 11b and opens a connection line from the electrode 13b, while the switch 29b grounds the electrode 12b and opens a connection line from the electrode 14b. Under this selected condition of the first sensor, when the A/F ratio of fuel mixture gas being supplied to the engine is in a lean region, as detected in the exhaust gas, an output level of the differential amplifier circuit 22 first becomes a positive level. The positive level voltage is supplied to a series circuit formed by the resistor 24 and the first oxygen pump element 15. As a result, pump current flows between the electrodes 11a and 11b of the first oxygen pump element 15. As the pump current flows from the electrode 11a to the electrode 11b, oxygen in the first gas residence chamber 2 is ionized at the electrode 11b, and moves into and through the first oxygen pump element 15. As a result, oxygen gas is discharged at the electrode 11a to pump out the oxygen in the first gas residence chamber 2.

When the oxygen in the first gas residence chamber 2 is pumped out, a difference in oxygen concentration is created between the exhaust gas in the first gas residence chamber 2 and the gas in the reference gas chamber 6. Owing to the difference in oxygen concentration, voltage $V_s$ is generated between the electrodes 12a and 12b of the cell element 16. The voltage $V_s$ is supplied to the inversion input terminal of the differential amplifier circuit 22. As the output voltage of the differential amplifier circuit 22 is a voltage proportion to voltage differential between the voltage $V_s$ and output voltage $V_{rl}$ of the reference voltage source 26, the pump current value is proportional to oxygen concentration in the exhaust gas.

In contrast, when the A/F ratio is in a rich region, the voltage $V_s$ exceeds the output voltage $V_{rl}$ of the reference voltage source 26. Accordingly, the output level of the differential amplifier circuit 22 is inverted from a positive level to a negative level. Owing to the low level, the pump current flowing between the electrodes 11a and 11b of the first oxygen pump element 15 is changed to invert the current direction. In other words, since the pump current flows from the electrode 11b to the electrode 11a, external oxygen is ionized at the electrode 11a and moves in the first oxygen pump element 15. As a result, oxygen gas is discharged at the electrode 11b into the first gas residence chamber 2, thus pumping oxygen into the first gas residence chamber 2. That is to say, as oxygen is pumped out and in by supplying the pump current so as to maintain the oxygen concentration in the first gas residence chamber 2 constant at all times, the pump current value $I_p$ and the output voltage of the differential amplifier circuit 22 are proportional to the oxygen concentration in the exhaust gas in the lean and rich region. The pump current $1_p$ is shown by a solid line a in FIG. 4.

The pump current value $I_p$ is given by the following equation.

$$I_p = 4e\sigma_0(P_{0exh} - P_{0v}) \quad (1)$$

Where, e is a charge; $\sigma_0$ is a diffusion coefficient for the exhaust gas by the induction hole 4; $P_{0exh}$ is an oxygen concentration in the exhaust gas; and $P_{0v}$ is an oxygen concentration in the first gas residence chamber 2.

Further, the diffusion coefficient $\sigma_0$ is given by the following equation:

$$\sigma_0 = DA/ktl \quad (2)$$

Where, A is the cross sectional area of the induction hole 4; k is a Boltzmann's constant; t is an absolute temperature; l is a length of the induction hole 4; and D is a diffusion constant.

Figure 4:
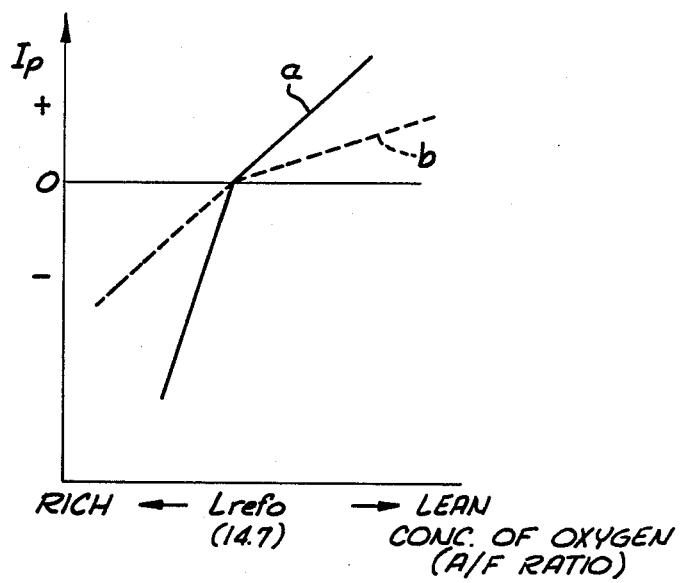
FIG. 4 is a graph showing the electric current output characteristics of the device of FIGS. 1-3.
Figure 5:
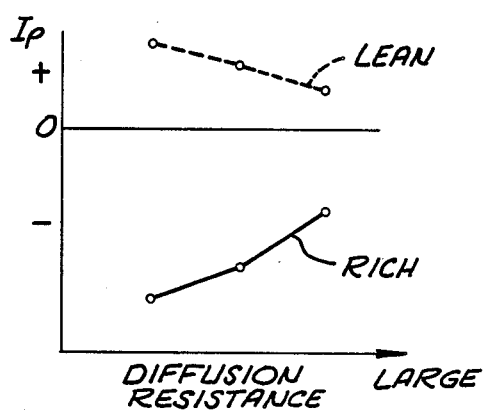
FIG. 5 is a graph showing the electric current output characteristics of the device of FIGS. 1-3 relative to the diffusion resistance.

In the next stage, a selected condition of the second sensor is provided in the following manner. That is to say, the switch 28a opens the connection line of the electrode 11a, and the switch 28b connects the electrode 13a with the current detection resistor 25. Further, the switch 29a grounds the electrode 13b, and opens the connection line of the electrode 11b, while the switch 29b grounds the electrode 14b, and opens the connection line of the electrode 12b. Under this selected condition of the second sensor, oxygen is pumped out and in by the same operation as in the selected condition of the first sensor as mentioned above, by supplying the pump current between the electrodes 13a and 13b of the second oxygen pump element 17 so as to maintain the oxygen concentration in the second gas residence chamber 3 constant at all times. Accordingly, the pump current value $I_p$ and the output voltage of the differential amplifier circuit 23 are proportional to the oxygen concentration in the exhaust gas in the lean and rich region. The pump current value $I_p$ under this selected condition of the second sensor may be given by the equation (1), wherein the diffusion coefficient $\sigma_0$, is defined by the combination of the induction hole 4 and the communication hole 5, and $P_{0v}$ is defined as an oxygen concentration in the second gas residence chamber 3. As is apparent from FIG. 5, the pump current value $I_p$ is decreased with an increase in diffusion resistance which is inversely proportional to the diffusion coefficient $\sigma_0$ in both the lean region and the rich region of the A/F ratio. Therefore, because the diffusion resistance under the selected condition of the second sensor is larger than that under the selected condition of the first sensor, the pump current value $I_p$ is smaller in both the lean region and the rich region as shown by a dotted line b in FIG. 4. To this end, as shown in FIG. 4, the characteristics of the pump current value in the rich region under the second sensor selected condition are substantially linearly continuous at $I_p = 0$ to the characteristics of the pump current value in the lean region under the first sensor selected condition which is accomplished by selecting an appropriate size and length for the communication hole 5. Further, characteristics of the output voltage of the differential amplifier circuits 22 and 23 are substantially linearly continuous at zero voltage.

Figure 6:
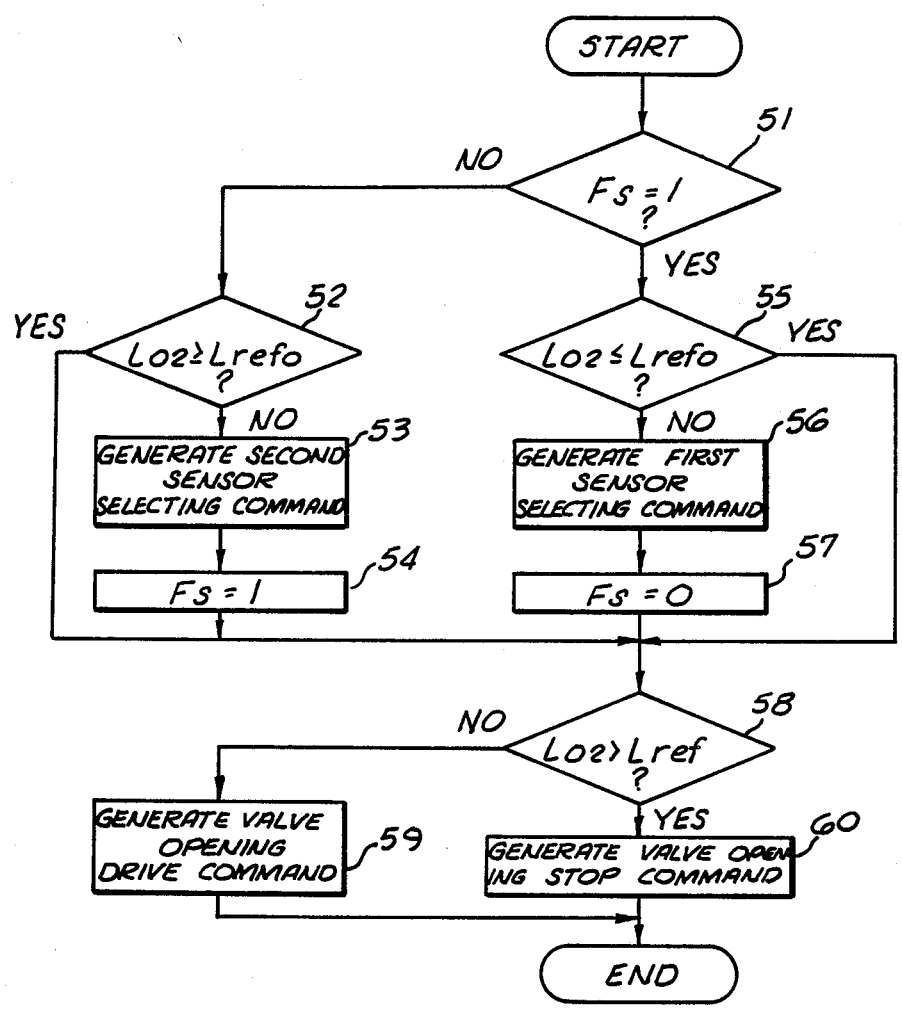
FIGS. 6 and 7 are flow charts showing the operation of the A/F ratio control circuit.

In the operation of the A/F ratio control circuit 32 for providing the linearly continuous output characteristics as mentioned above, referring to FIG. 6, it is determined whether or not a flag $F_s$ for representing the first and second sensor selected condition is equal to "1⇌ (step 51). If $F_s = 0$, the first sensor is in the selected condition, and therefore the pump current value $I_p(1)$ of the first sensor to be generated by the A/D converter 31 is read. Then, it is determined whether or not an oxygen concentration detection output value $L_{o2}$ corresponding to the oxygen pump cell current value $I_p(1)$ is equal to or greater than a reference value $L_{ref0}$ corresponding to zero voltage of the output voltage $V_{s1}$ of the differential amplifier circuit 22 (step 52). If $L_{o2} \geq L_{ref0}$ ($V_{s1} \geq 0$), the A/F ratio is in the lean region, and therefore the first sensor selected condition is retained. If $L_{o2} < L_{ref0}$ ($V_{s1} < 0$), the A/F ratio is in the rich region, and therefore a second sensor selecting command is generated to the drive circuit 30 (step 53). Then, the flag $F_s$ is set at "1", so as to represent that the second sensor has been selected (step 54). On the other hand, if at the start $F_s = 1$, the second sensor is in the selected condition, and therefore the pump current value $I_p(2)$ of the second sensor to be generated by the A/D converter 31 is read. Then, it is determined whether or not the oxygen concentration detection output value $L_{o2}$ corresponding to the pump current value $I_p(2)$ is equal to or less than the reference value $L_{ref0}$ corresponding to zero voltage of the output voltage $V_{s2}$ of the differential amplifier circuit 23 (step 55). If $L_{o2} \leq L_{ref0}$ ($V_{s2} \leq 0$), the A/F ratio is in the rich region, and therefore the second sensor selected condition is retained. If $L_{o2} > L_{ref0}$ $V_{s2} > 0$), the A/F ratio is in the lean region, and therefore a first sensor selecting command is generated to the drive circuit 30 (step 56). Then, the flag $F_s$ is set at "0", so as to represent that the first sensor has been selected (step 57). The drive circuit 30 drives the switches 28a, 28b, 29a and 29b to the first sensor selected position according to the first sensor selecting command, and such a driving condition is maintained until the second sensor selecting command is supplied from the A/F ratio control circuit 32. Similarly, the drive circuit 30 drives the switches 28a, 28b, 29a and 29b to the second sensor selected position according to the second sensor selecting command, and such a driving condition is maintained until the first sensor selecting command is supplied from the A/F ratio control circuit 32. When the first or second sensor is selected in this manner, the A/F ratio control circuit 32 determines whether or not the oxygen concentration detection output value $L_{o2}$ by the first or second sensor to be generated by the A/D converter 31 is greater than a target value $L_{ref}$ corresponding to a target A/F ratio (step 58). If $L_{o2} \leq L_{ref}$, the A/F ratio of the supplied mixture gas is rich, and therefore a drive command for opening the electromagnetic valve 34 is generated to the drive circuit 33 (step 59). If $L_{o2} > L_{ref}$, the A/F ratio of the supplied mixture gas is lean, and therefore a stop command for stopping the drive of opening the electromagnetic valve 34 is generated to the drive circuit 33 (step 60). The drive circuit 33 drives to open the electromagnetic valve 34 according to the drive command to supply a secondary air to the engine intake manifold, thus making the A/F ratio lean. Further, the drive circuit 33 stops the drive of opening the electromagnetic valve 34 according to the stop command to make the A/F ratio rich. Such operation is repeatedly executed every predetermined period to control the A/F ratio of the supplied mixture gas to the target A/F ratio. Although the reference value $L_{ref0}$, that is, the determination reference voltages of the voltages $V_{s1}$ and $V_{s2}$ are set at zero, the determination reference voltage of the voltage $V_{s1}$ may be set at a value slightly smaller than zero, and that of the voltage $V_{s2}$ may be set at a value slightly greater than zero, so as to provide a hysteresis.

Figure 7:
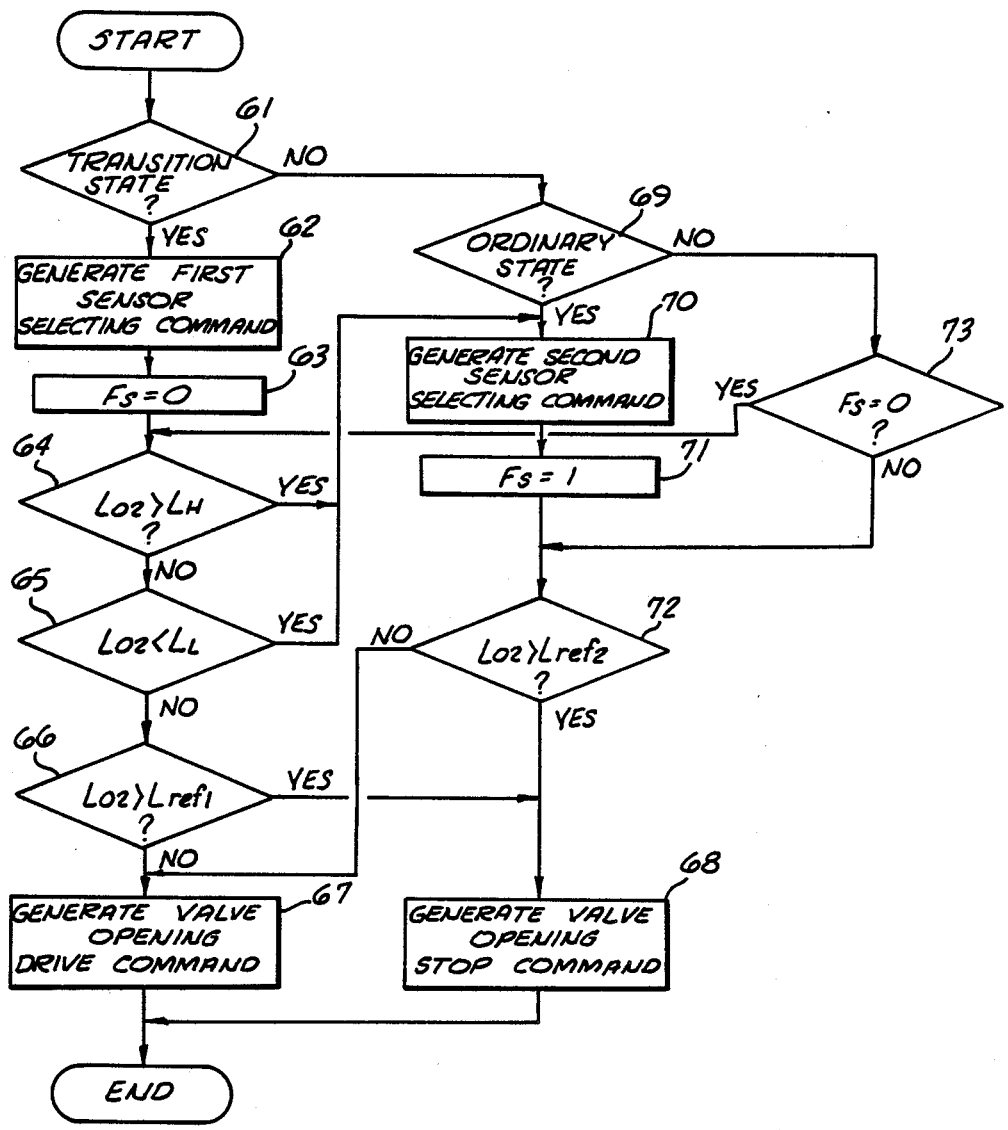

FIG. 7 shows another operation flow of the A/F ratio control circuit 32 employing the oxygen concentration detector of the present invention as shown in FIGS. 1, 2 and 3. In this case, it is first determined whether or not the engine is in a transition state according to an output level of a plurality of operation parameter detecting sensors (step 61). In a transition state such as acceleration, as detected by the operation parameter detecting sensors (not shown), the first sensor selecting command is generated to the drive circuit 30 for the purpose of improving the speed of response (step 62) and the flag $F_s$ is set to "0" so as to represent that the first sensor has been selected (step 63). Then, the pump current value $I_p(1)$ of the first sensor to be generated by the A/D converter 31 is read, and it is determined whether or not the oxygen concentration detection output value $L_{o2}$ corresponding to the pump current value $I_p(1)$ is greater than an upper limit $L_H$ or is smaller than a lower limit $L_L$ (steps 64 and 65). If $L_L \leq L_{o2} \leq L_H$, the A/F ratio of the supplied mixture gas is neither overlean nor overrich, and therefore it is determined whether or not the oxygen concentration detection output value $L_{o2}$ of the first sensor is greater than a target value $L_{ref1}$ corresponding to a target rich A/F ratio which is smaller than a theoretical A/F ratio (step 66). If $L_{o2} \leq L_{ref1}$, the A/F ratio of the supplied mixture gas is richer than the target rich A/F ratio, and therefore the drive command for opening the electromagnetic valve 34 is generated to the drive circuit 33 (step 67). If $L_{o2} > L_{ref1}$, the A/F ratio of the supplied mixture gas is leaner than the target rich A/F ratio, and therefore the stop command for stopping the drive of opening the electromagnetic valve 34 is generated to the drive circuit 33 (step 68).

On the other hand, if the engine is not in a transition state, it is determined whether or not the engine is in a steady operating state according to the output level of the plurality of operation parameter detecting sensors (step 69). As accurate control of the A/F ratio is desired in the steady-state for the purpose of improving exhaust gas purification performance, the second sensor selecting command is generated to the drive circuit 30 (step 70), and the flag $F_s$ is set to "1" so as to represent that the second sensor has been selected (step 71). If $L_{o2} < L_L$ or $L_{o2} > L_H$ in steps 64 and 65, the A/F ratio is overlean or overrich, respectively, and therefore step 70 is executed to select the second sensor for the purpose of preventing generation of "blackening" which is caused by excessive current being supplied through the electrolyte to produce a black color and damage. Then, the pump current value $I_p(2)$ of the second sensor to be generated by the A/D converter 31 is read and it is determined whether or not the oxygen concentration detection output value $L_{o2}$ corresponding to the pump current value $I_p(2)$ is greater than a target value $L_{ref2}$ corresponding to a target lean A/F ratio which is greater than the theoretical A/F ratio (step 72). If $L_{o2} \leq L_{ref2}$, the A/F ratio of the supplied mixture gas is richer than the target lean A/F ratio, and therefore the drive command for opening the electromagnetic valve 34 is generated to the drive circuit 33 (step 67). If $L_{o2} > L_{ref2}$, the A/F ratio of the supplied mixture gas is leaner than the target lean A/F ratio, and therefore the stop command for stopping the drive of opening the electromagnetic valve 34 is generated to the drive circuit 33 (step 68).

If the engine is not in the steady state, it is determined whether or not the flag $F_s$ is set at "0" (step 73). If $F_s = 0$, the step 64 is executed, while if $F_s = 1$, the step 72 is executed. Such operation is repeatedly executed every predetermined period, such as once every second, to control the A/F ratio to the target rich A/F ratio in the transition state and to the target lean A/F ratio in the ordinary state.

Figure 8:
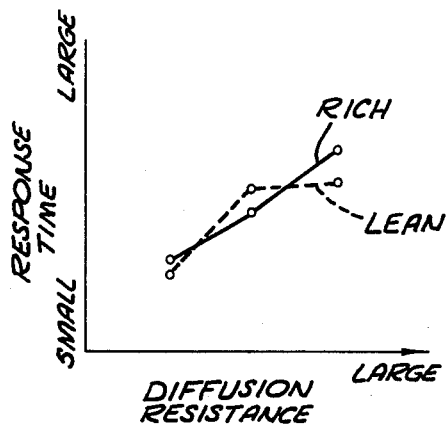
FIGS. 8, 9 and 10 are graphs showing various relationships regarding the diffusion resistance.

According to the oxygen concentration detector of the present invention, the speed of response is improved in both the rich and lean regions of the A/F ratio as the diffusion resistance by the induction hole 4 and the communication hole 5 is decreased as shown in FIG. 8. Therefore, good drivability may be secured by selecting the first sensor having a small diffusion resistance in the transition state.

Figure 9:
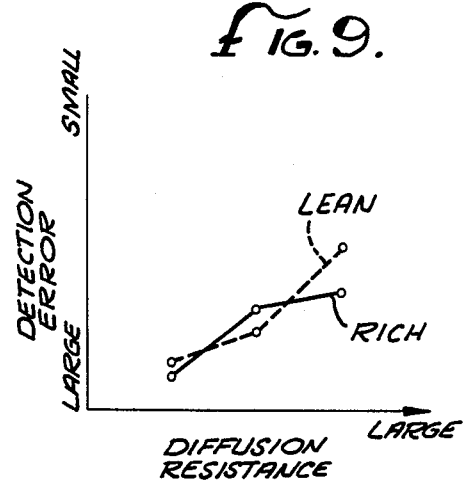

On the other hand, as shown in FIG. 9, oxygen concentration detection error is reduced in both the rich and lean regions of the A/F ratio as the diffusion resistance is increased. This is due to the fact that any influence on the oxygen concentration detection by exhaust gas temperature, exhaust gas pulsation and exhaust gas flow rate is reduced as the diffusion resistance is increased. Accordingly, the A/F ratio of the supplied mixture gas may be controlled to the target A/F ratio with a high accuracy to improve the exhaust gas purification performance by selecting the second sensor having a large diffusion resistance in the ordinary state.

Figure 10:
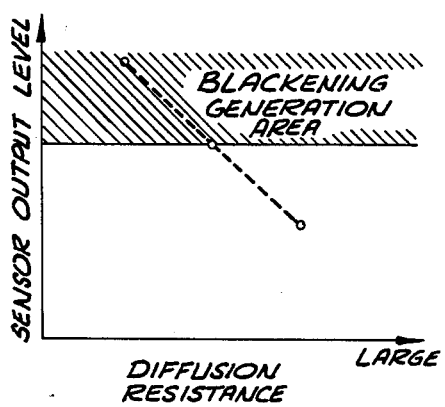

As shown in FIG. 10, when the A/F ratio is overlean under a certain operational condition, and the diffused resistance is small, the pump current value falls in a region where blackening will be generated. This also applies to the case when the A/F ratio is overrich. Accordingly, generation of the blackening may be avoided by selecting the second sensor having a large diffusion resistance which results in a lower current in the overlean or overrich A/F ratio, thereby preventing rapid deterioration of the oxygen pump element and the cell element.

The oxygen concentration detector of this invention permits a still further improvement in its detecting capabilities and accuracy by the use of an abnormality detection and correction system to correct for certain abnormalities that may occur in the detector. Specifically, it has been found that after extended use in the exhaust gas system of an internal combustion engine the induction hole 4 will become more restricted by the deposit of oxides in the hole and, to a lesser extent, lead deposits. Further, occasionally the induction hole 4 may become enlarged abruptly by a portion of the deposited oxides or other materials breaking away whereby the effective diffusion restriction of hole 4 is abruptly decreased. The occurrence of either an increase or decrease in the diffusion restriction of hole 4 effectively changes the diffusion coefficient and therefore, as shown by the above formula (1), the current produced whereby an inaccurate indication of A/F will be produced. However, by this invention there is provided an A/F ratio detection correcting routine shown in FIG. 11 and an A/F ratio control routine shown in FIG. 12 for the A/F ratio control circuit 32 are sequentially executed according to a clock pulse. In the A/F ratio detection correcting routine, the A/F ratio control circuit 32 first determines whether or not the engine is in a predetermined operational condition according to an output level of a plurality of operation parameter detecting sensors (step 61). The predetermined operational condition is a stable operational condition such as an idling or ordinary operational condition. If such a predetermined operational condition is detected, it is then determined whether or not an A/F ratio is controlled to a target A/F ratio, and has been stabilized (step 62). When the A/F ratio is controlled to the target A/F ratio, and is stabilized, fluctuation in the detection value of oxygen concentration by the first sensor or the second sensor is reduced, and the magnitude of fluctuation falls in a predetermined range. Therefore, when the fluctuation range of the detection value of oxygen concentration by the sensor selected becomes equal to or less than a predetermined value, and a predetermined time has elapsed, it is regarded that the A/F ratio has been stabilized. When the A/F ratio is in a stabilized condition, A/F ratio feedback (F/B) control according to the detecting output of oxygen concentration by the first or second sensor is stopped (i.e. execution of the normal A/F ratio control routine is stopped), and instead a predetermined valve opening drive command and a valve opening stop command are generated so as to open the electromagnetic valve 34 with a predetermined duty ratio every predetermined period of time to thereby make the A/F ratio constant (step 63). While the system is operating under this condition, it is determined whether or not a flag $F_s$ for representing a selected condition of the first and second sensors is "1" (step 64). If $F_s=0$, the first sensor is in the selected condition, and therefore the pump current value $I_p(1)$ of the first sensor to be generated by the A/D converter 31 is read to be stored in a storage position $A_1$ of an internal memory (not shown) (step 65). Then, a second sensor selecting command is generated to the drive circuit 30 to obtain a second sensor selected condition (step 66) and the pump current value $I_p(2)$ of the second sensor to be generated by the A/D converter 31 is read to be stored in a storage position $A_2$ of the internal memory (step 67). Thereafter, to obtain the first sensor selected condition again, a first sensor selecting command is generated to the drive circuit 30 (step 68), and the pump current value $I_p(1)$ of the first sensor to be generated by the A/D converter 31 is read to be stored in a storage position $A_3$ of the internal memory (step 69). On the other hand, if $F_s=1$, the second sensor is in the selected condition, and therefore the pump current value $I_p(2)$ of the second sensor to be generated by the A/D converter 31 is read to be stored in the storage position $A_1$ of the internal memory (step 70). Then, the first sensor selecting command is generated to the drive circuit 30 to obtain the first sensor selected condition (step 71), and the pump current value $I_p(1)$ of the first sensor to be generated by the A/D converter 31 is read to be stored in the storage position $A_2$ of the internal memory (step 72). Thereafter, to obtain the second sensor selected condition again, the second sensor selecting command is generated to the drive circuit 30 (step 73), and the pump current value $I_p(2)$ of the second sensor to be generated by the A/D converter 31 is read to be stored in the storage position $A_3$ of the internal memory (step 74). In the next step, to determine again whether or not fluctuation in the detection value of oxygen concentration is small, the pump current values $I_p(1)$ or $I_p(2)$ are read from the storaqe positions $A_1$ and $A_3$ of the internal memory to calculatean absolute value $\Delta I_p$ of the difference between the pump current values $I_p(1)$ or the pump current values $I_p(2)$ (step 75), and determine whether or not the absolute value $\Delta I_p$ is equal to or less than a predetermined value $\Delta I_{pr}$ (step 76). If $\Delta I_p \leq \Delta I_{pr}$, correction factors $K_{COR1}$ and $K_{COR2}$ which will be hereinafter described are calculated according to the equations as given below (step 77). but if $\Delta I_p > \Delta I_{pr}$, which indicates that the engine operation is not stabilized, the A/F ratio control according to the detection output of oxygen concentration by the sensor selected is carried out again (i.e. execution of the normal A/F ratio control routine) (step 78).

The correction factor $K_{COR1}$ for correcting the oxygen concentration detection value $L_{o2}(1)$ of the first sensor is calculated from the following equation.

$$K_{COR1} = C/(I_p(1)/I_p(2)-1) \qquad (3)$$

The correction factor $K_{COR2}$ for correcting the oxygen concentration detection value $L_{o2}(2)$ of the second sensor is calculated from the following equation.

$$K_{COR2}+(K_{COR1}+C)/(1+C) \qquad (4)$$

Where, C represent $I_p(1)/I_p(2)-1$ before a change in output characteristics.

Then, it is determined whether or not the correction factors $K_{COR1}$ and $K_{COR2}$ calculated are equal to or greater than a predetermined value $K_1$ and equal to or greater than a predetermined value $K_2$ (step 79). If $K_1 \leq K_{COR1} \leq K_2$ or $K_1 \leq K_{COR2} \leq K_2$, the A/F ratio control according to the oxygen concentration detection value of the sensor selected is carried out again (step 78). If $K_{COR1} < K_1$, $K_{COR1} > K_2$, $K_{COR2} < K_1$, $K_{COR2} > K_2$, an alarm is generated to alert the driver by turning on a lamp, for example, since the change in the output characteristics is large, and good A/F ratio feedback control may not be expected even if correction by the present invention is carried out (step 80).

Figure 12:
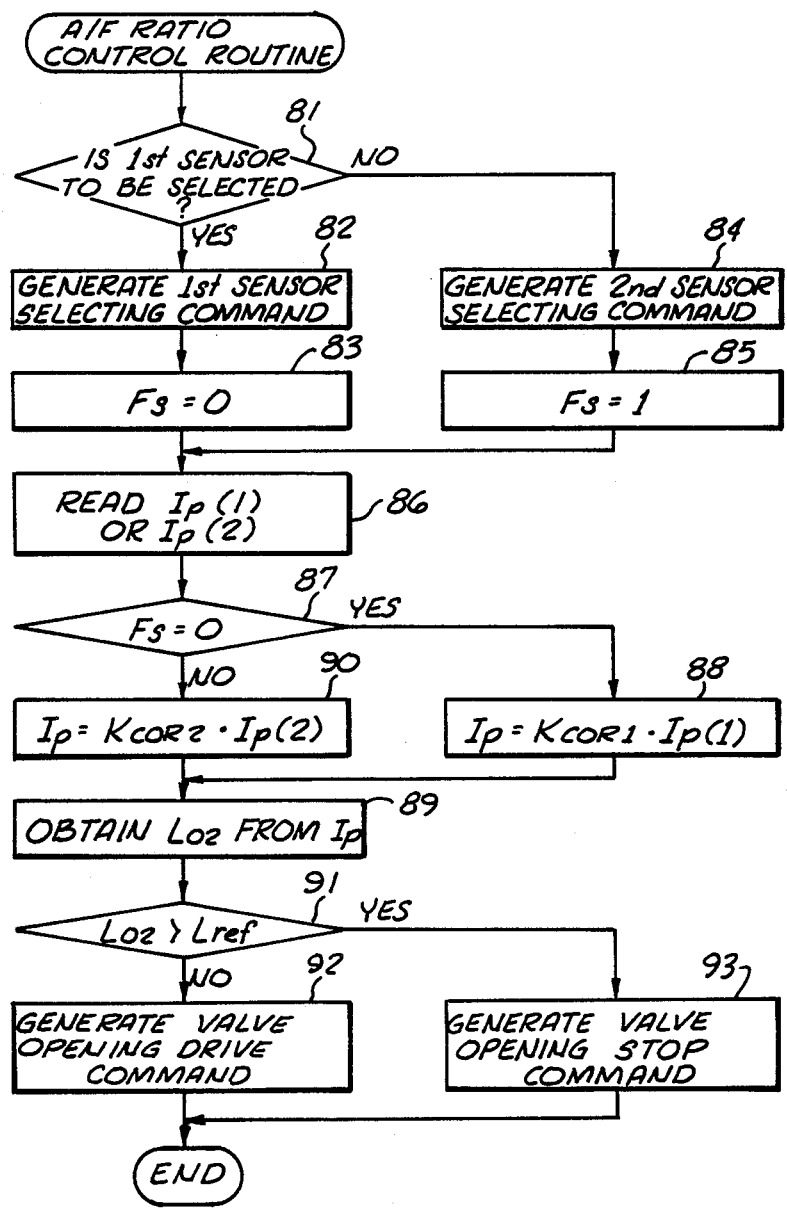

Referring to FIG. 12, which shows the A/F ratio control routine, it is first determined which of the first and second sensors should be selected (step 81). Such selection of the first sensor or the second sensor is determined according to operational condition of the engine or control region of A/F ratio. If it is determined that the first sensor should be selected, the first sensor selecting command is generated to the drive circuit 30(step 82), and the flag $F_s$ is set to "0" so as to represent that the first sensor has been selected (step 83). On the other hand, if it is determined that the second sensor should be selected, the second sensor selecting command is generated to the drive circuit 30(step 84), and the flag $F_s$ is set to "1" so as to represent that the second sensor has been selected (step 85). The drive circuit 30 drives the switches 28a, 28b, 29a and 29b to the first sensor selected position according to the first sensor selecting command, and such a driving condition is retained until the second sensor selecting command is supplied from the A/F ratio control circuit 32. Further, the drive circuit 30 drives the switches 28a, 28b, 29a and 29b to the second sensor selected position according to the second sensor selecting command, and such a driving condition is retained until the first sensor selecting command is supplied from the A/F ratio control circuit 32.

Next, the pump current value $I_p(1)$ or $I_p(2)$ generated by the A/D converter 31 is read (step 86), and it is determined whether or not the flag $F_s$ is "0" (step 87). If $F_s=0$, the first sensor is in the selected condition, and therefore the pump current value $I_p(1)$ as read is multiplied by the correction factor $K_{COR1}$ (step 88) to obtain the corresponding oxygen concentration detection value $L_{o2}$ (step 89). If $F_s=1$, the second sensor is in the selected condition, and therefore the pump current value $I_p(2)$ as read is multiplied by the correction factor $K_{COR2}$(step 90) to obtain the corresponding oxygen concentration detection value $L_{o2}$ (step 89). Then, it is determined whether or not the oxygen concentration detection value $L_{o2}$ is greater than a target value $L_{ref}$ corresponding to the target A/F ratio (step 91). If $L_{o2} \leq L_{ref}$, the A/F ratio of supplied mixture gas is rich, and therefore a drive command for opening the electromagnetic valve 34 is generated to the drive circuit 33 (step 92). If $L_{o2} > L_{ref}$, the A/F ratio of supplied mixture gas is lean, and therefore a stop command for stopping the drive of opening the electromagnetic valve 34 is generated to the drive circuit 33 (step 93). The drive circuit 33 drives to open the electromagnetic valve 34 according to the drive command to supply a secondary air to the engine intake manifold, thus making the A/F ratio lean. Further, the drive circuit 33 stops the drive of opening the electromagnetic valve 34 according to the stop command to make the A/F ratio rich. Such operation is repeatedly executed every predetermined period to control the A/F ratio of the supplied mixture gas to the target A/F ratio.

Figure 11:
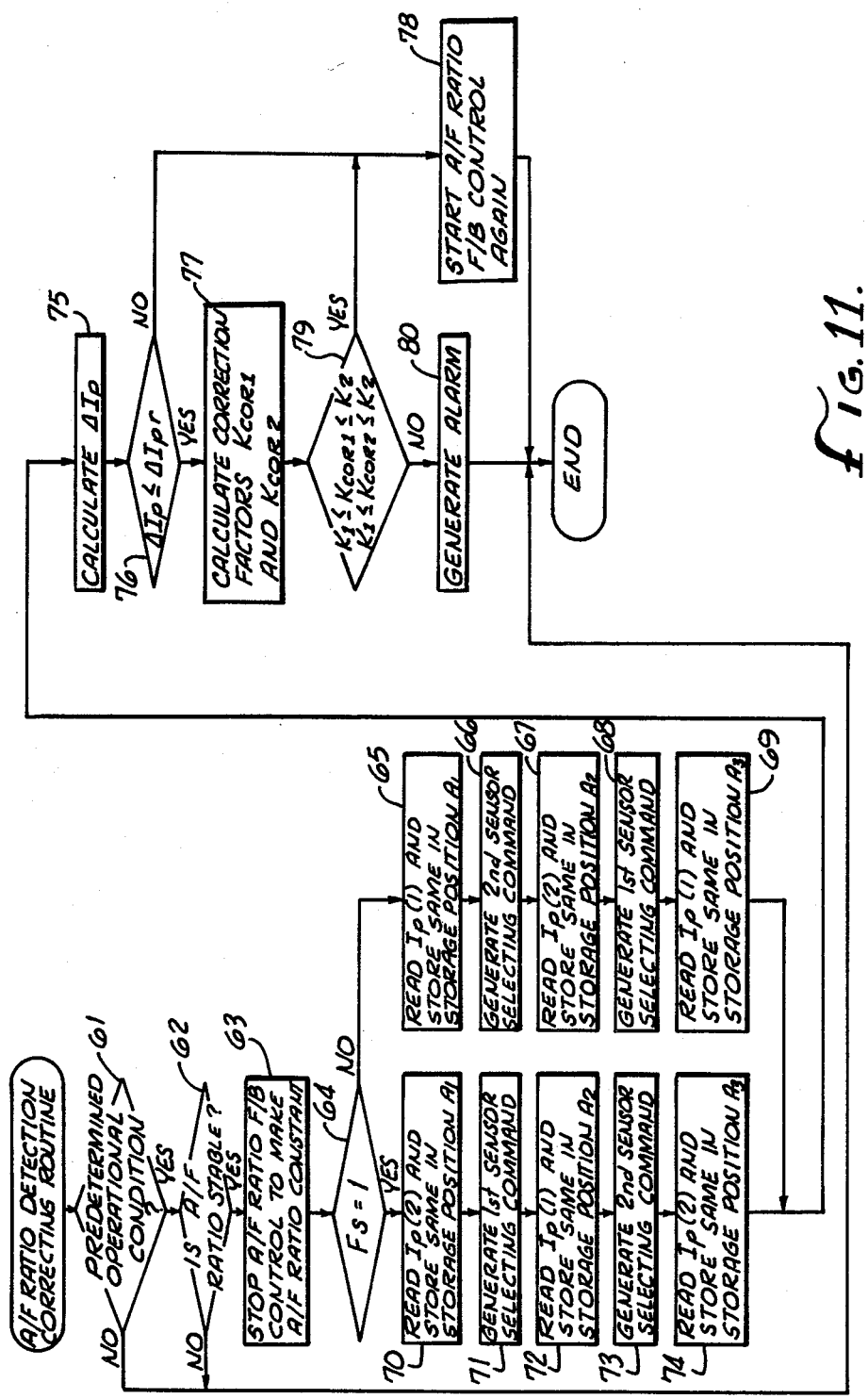
FIGS. 11 and 12 are flow charts showing the operation of the A/F ratio detection correction and control routines of the present invention.

Thus, the two cell chamber oxygen concentration detection device of this invention permits the A/F ratio detection correcting routine and control routine of FIGS. 11 and 12, respectively, to periodically correct the readings that result from the cells that would otherwise be incorrect since the readings from the cells of the two chambers can be compared to each other and to a stabilized operating condition. Normally, in the embodiment of FIG. 2, the second chamber 3 cells 17 and 18 provide a more accurate reading for a longer period of time since the diffusion hole 5 is not as susceptible to clogging or damage as diffusion hole 4. Moreover, cells 17 and 18 are operated at substantially lower current levels, as a result of the diffusion coefficient, whereby they are not affected by changes in the induction hole 4 as are the first pair of cells 15 and 16.

Although the entire description of the invention thus far has been in connection with the oxygen concentration detector shown in FIGS. 1 and 2 and the circuit shown in FIG. 3, there are various other configurations of detectors and circuits that are also within the present invention and have the advantages and functional capabilities set forth above. Next we will describe additional detector configurations and then additional circuits. To the extent these embodiments are the same as previously described with respect to FIGS. 1-3, those descriptions will not be repeated but rather only the differences will be described.

Although the induction hole 4 is employed as a first gas diffusion restricting means and the communication hole 5 is employed as a second gas diffusion restricting means in the preferred embodiment of FIG. 2 of the present invention, as an alternative a gap may be formed between both the first pair of electrodes in the first gas residence chamber 2 as shown in FIG. 13 which gap becomes the induction hole 4, and the communication hole 5 to the second gas residence chamber 3 is merely the space between the walls. Further, as shown in FIG. 14, as hole 5 may be of a larger size and filled with porous materials 38 and 40 such as alumina ($Al_2O_3$) to form a porous diffusion layer, which makes the cells less influenced by temperature changes and other factors.

Figures 17, 18:
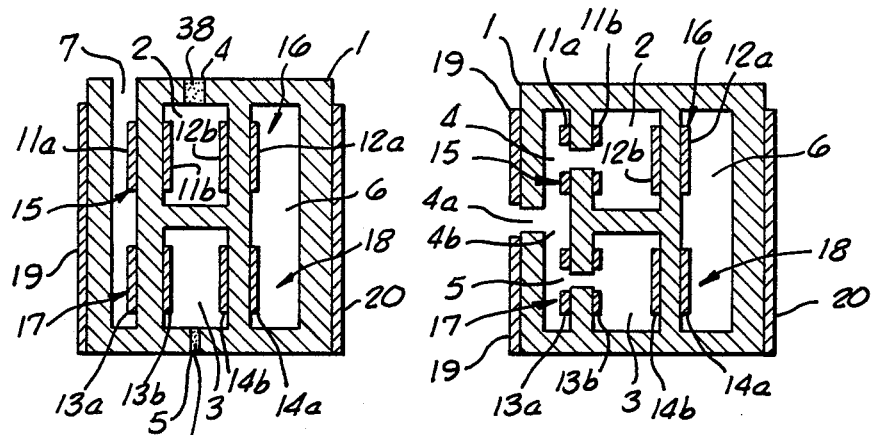

Referring now to FIGS. 15, 16 and 17, alternative arrangements of the first and second gas residence chambers 2 and 3 and the diffusion restriction holes 4 and 5 are shown wherein the first and second gas residence chambers 2 and 3 are arranged in a "parallel" gas flow arrangement, that is, the holes 4 and 5 separately communicate with the gas to be analyzed, such as the exhaust gas, rather than hole 5 only communicating the second chamber 3 with the first chamber 2 to provide a "series" flow. The holes 4 and 5 in the embodiments of FIGS. 15, 16 and 17 produce two different diffusion coefficients so that the cells in the two chambers respond differently, i.e. the cells in the first chamber with greater speed and the cells in the second chamber with greater accuracy. Thus, the hole 4 in the device of FIG. 15 is larger than hole 5 to provide less diffusion resistance. Similarly, the gap or hole 4 in the device of FIG. 16 is larger or less restrictive than the gap or hole 5, and the porous material 38 and hole 4 in the device of FIG. 17 form less of a diffusion restriction than the porous material 40 and hole 5. In all other respects the devices of FIGS. 15, 16 and 17 are constructed and function in the same manner as described above with respect to the detectors of FIGS. 2, 13 and 14, respectively.

Figure 19:
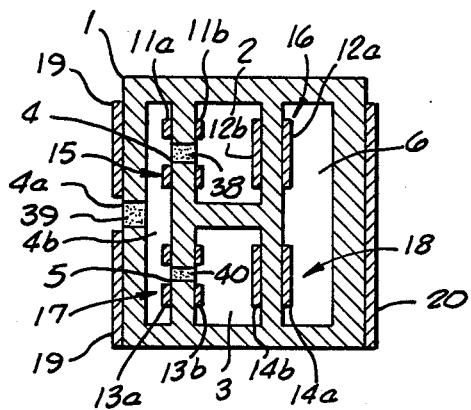

Similarly, two more alternative embodiments of the oxygen concentration detector are shown in FIGS. 18 and 19 wherein there is a combination of "series" and "parallel" gas flow. As shown in those figures, the gas to be analyzed, such as exhaust gas, is introduced into the first gas residence chamber 2 through a first diffusion hole 4a, an introduction chamber 4b and a second diffusion restriction hole 4, and the gas is introduced into the second gas residence chamber 3 through the same hole 4a and introduction chamber 4b and then through a third diffusion restriction hole 5. Again, the hole 4 provides less of a diffusion restriction to the first chamber 2 than the hole 5 provides to the second chamber 3. Each of the electrodes 11a, 11b, 13a and 13b is provided with a hole in the middle to expose the holes 4 and 5. The holes 4, 4a and 5 of the device of FIG. 19 are provided with a porous material 38, 39 and 40, respectively. In all other respects the devices of FIGS. 18 and 19 are the same as the comparable devices of FIGS. 2, 14, 15 and 17, and the components are identically numbered.

Figure 20:
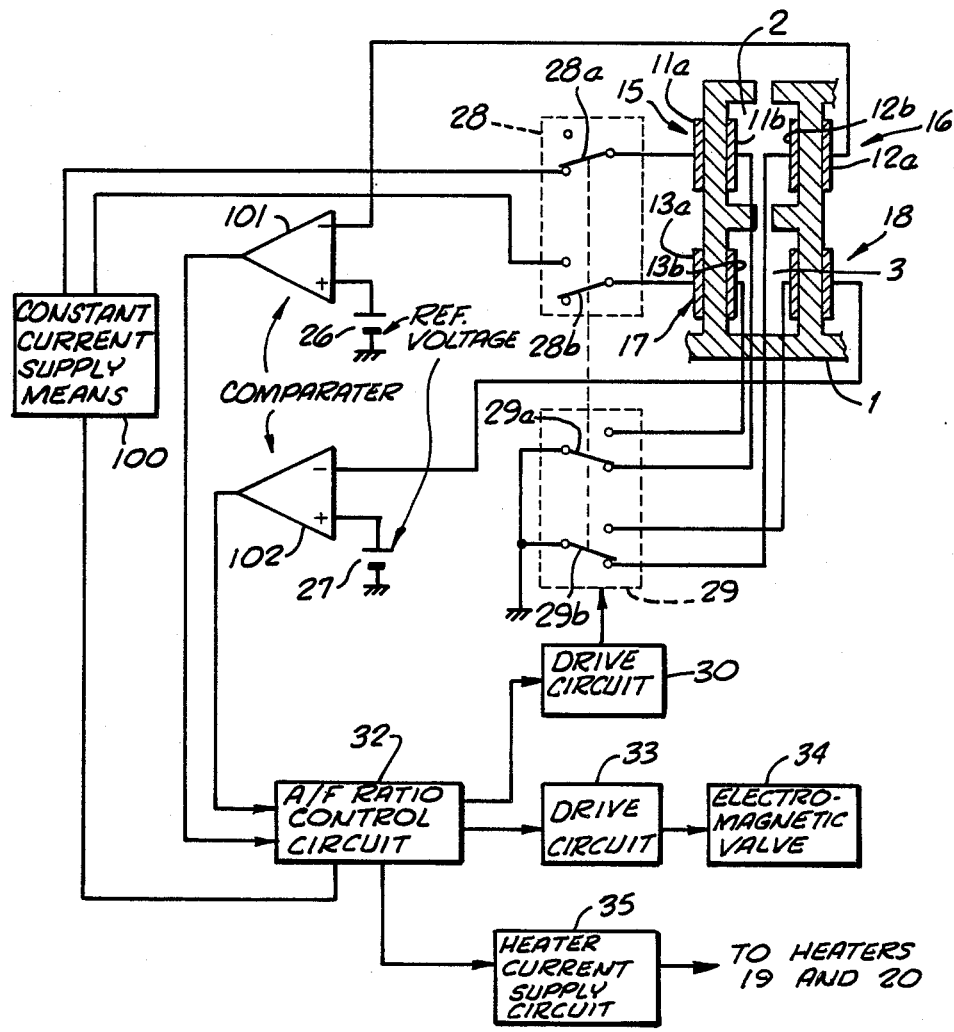
FIG. 20 is a circuit diagram similar to FIG. 3 of a modified form of A/F ratio control circuit of this invention.

Referring now to FIG. 20, the alternative circuit shown is similar to but simpler than the circuit of FIG. 3. To the extent the components and their functions are the same in the two circuits, the same numerals have been used and they will not be redescribed in detail here. Again, selector circuits 28 and 29 are provided and operated by drive circuit 30 to switch between the cells in the first chamber 2 and the second chamber 3. A source 100 of constant electrical current supply is connected to the selector circuit 28 for selectively supplying a predetermined constant electrical current to one or the other of the oxygen pumping cells 15 and 17 with the selection being made by the A/F ratio control circuit 32. Comparators 101 and 102 are connected to the cell elements 16 and 18, and reference voltage sources 26 and 27, respectively, for periodically determining whether the A/F ratio is rich or lean. The constant current in the selected pumping element 15 or 17 will result in a voltage that varies with the A/F ratio, which voltage is compared by comparator 101 o 102 with the reference voltage 26 or 27 and with a target voltage whereby it is determined whether the A/F ratio is rich or lean. In all other respects the system of FIG. 20 functions in the same manner as the system of FIG. 3 and has most of the same features, although it is not as precise in measuring. One feature of being simpler is that the system of FIG. 20 does not require adjustment of the electrical feed back system.

Figure 21:
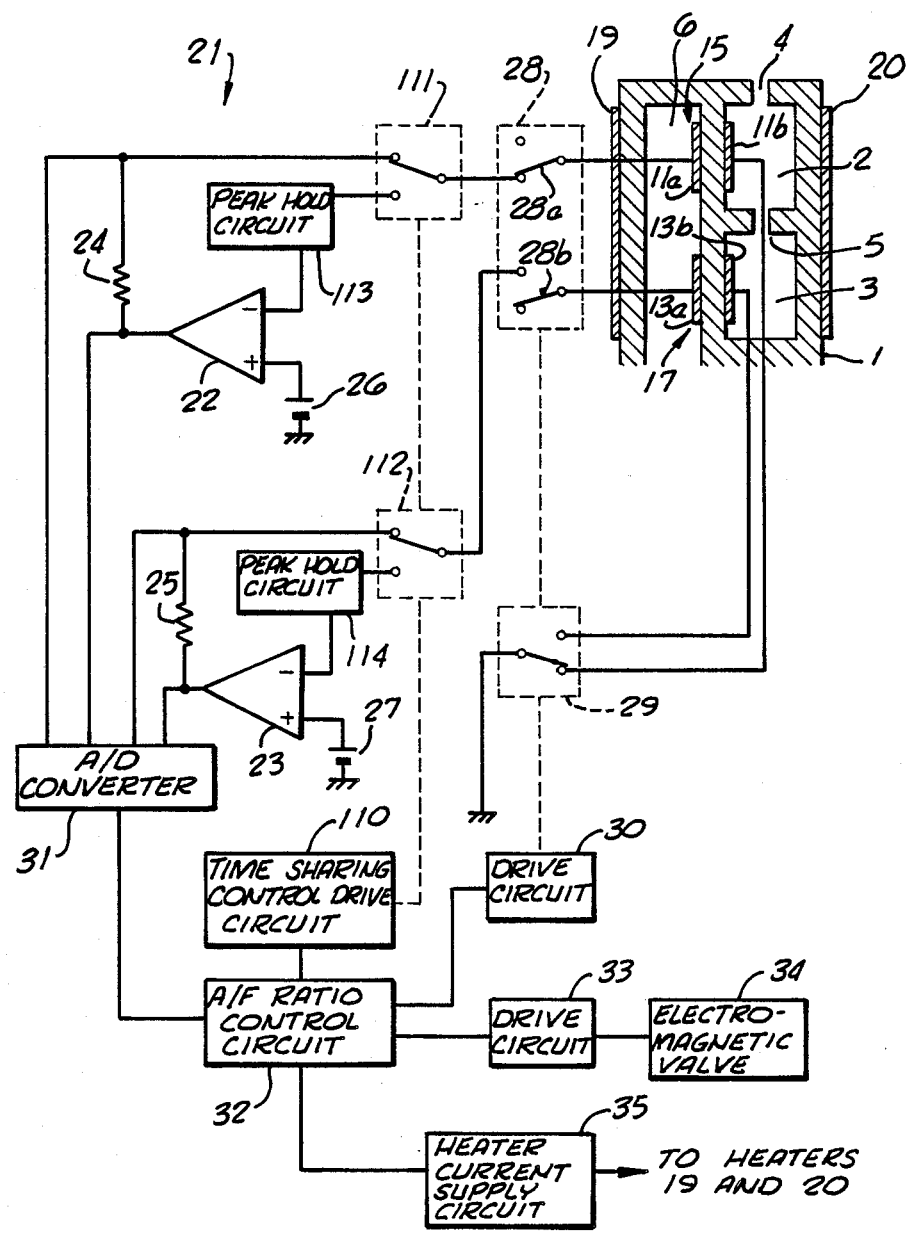
FIGS. 21 and 22 are circuit diagrams similar to FIGS. 3 and 20 of modified forms of the A/F ratio control circuit and a modified form of the oxygen concentration detector of this invention.

Referring to FIG. 21, another control circuit similar to FIG. 3 is shown which is simpler in some respects and employs a simplified oxygen concentration detector 1. The system of FIG. 21 uses the so-called concept of "time-sharing" wherein the cells perform different functions at different times. Specifically, the detector 1 has the two separate gas residence chambers 2 and 3 but each chamber has only one cell, namely cells 15 and 17, respectively. The outside electrodes 11a and 13a are exposed to a chamber 6 having a source of reference gas, such as air, rather than to the exhaust gas. By appropriate switching each cell 15 and 17 functions at one time as an oxygen pumping cell (the same as previously described cells 15 and 17) and another time as a sensing cell element (the same as previously described cells 16 and 18) which is accomplished by the time sharing drive circuit 110 and switches 111 and 112. Peak hold circuits 113 and 114 are provided between the cells 15 and 17 and the differential amplifier circuits 22 and 23, all respectively. One of the cells 15 or 17 detects the voltage of the electromotive force being produced, similar to cells 16 and 18, and then current is supplied to the same cell to function as an oxygen pump, with the polarity of that current being determined by the level of the voltage difference between the reference voltage and the peak hold voltage. The value of the current supplied to the oxygen pump cell is measured and relates to the A/F ratio which then is used by the A/F ratio control circuit 32 to operate the secondary air control valve 34 by drive circuit 33 in the same manner as previously described. The peak hold circuits 113 and 114 served to hold a particular mode of operation of the cell that has been selected for a short duration relative to the normal mode of operation, such as about one-fifth of the time.

Figure 22:
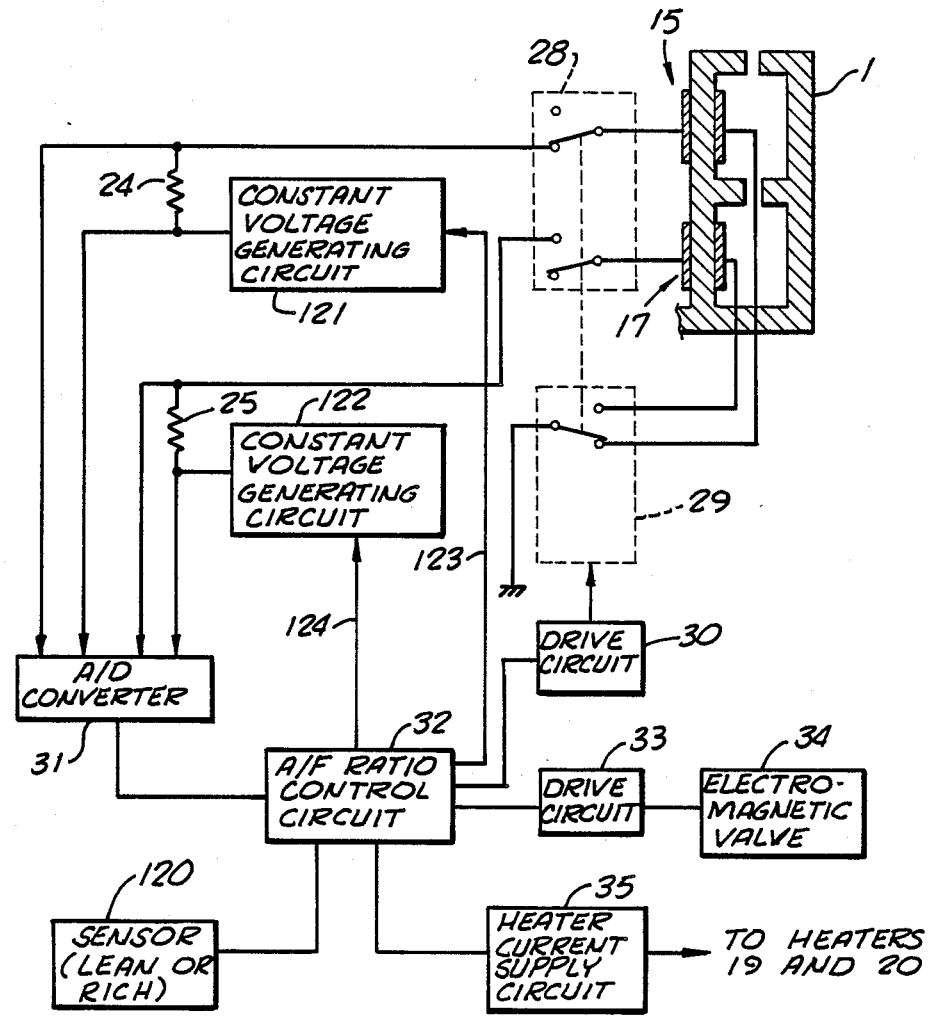

Referring now to FIG. 22, another alternative control circuit similar to FIG. 3 is shown but which is simpler in many respects. The system of FIG. 22 also uses the simplified detector 1 shown in FIG. 21 having only one pair of electrodes for each chamber 2 and 3 for the same reasons and in the same manner. The circuit of FIG. 22 differs from that of FIG. 21 in that a conventional sensing means 120 is employed to detect whether the A/F ratio is rich or lean, which means 120 may be a titanium type sensor, a lambda type sensor, or even means for sensing various operating parameters of the engine for making that rich/lean determination. The appropriate cell 15 or 17 is selected by the A/F ratio control circuit 32 operating the drive circuit 30 to operate switch circuits 28 and 29 in the same manner and for the same reasons previously described. Constant voltage generating circuits 121 and 122 are provided with the cells 15 and 17, respectively, and serve to impose a predetermined constant voltage to the selected cell 15 or 17 to function as an oxygen pump. The polarity of the applied voltage is selected on the basis of the determination of whether the A/F ratio is rich or lean as made by the sensor 120 and this signal of selected polarity is supplied from the control circuit 32 to the circuits 121 and 122 through conductors 123 and 124, respectively. The results current in the selected cell 15 or 17 is then measured and converted to a valve of A/F ratio which is then used by the A/F ratio control circuit to operate the drive circuit 33 and valve 34 of the secondary air system, all as described with respect to FIG. 3.

Although the A/F ratio of the supplied mixture gas is controlled to the target A/F ratio by supplying a secondary air according to an output from the first or second sensor in each of the described embodiments of the present invention, the A/F ratio ma be controlled by regulating the amount of supplied fuel according to the output from the first or second sensor.

As is described above, the oxygen concentration detector of the present invention is provided with the first and second gas residence chambers having different diffused resistances to a gas to be analyzed, such as an exhaust gas, that is induced therein, both chambers are communicated with the gas to be analyzed through a gas diffusion restricting means with two different diffusion coefficients and normally is further provided with first and second pairs of electrodes mounted on inside and outside surfaces of electrolyte wall portions of the first and second gas residence chambers in such a manner that each electrode is arranged in opposed relation with respect to the electrolyte wall portions, although it is possible to employ only one pair of electrodes for each chamber by providing other circuit and sensing means. With this arrangement, it is possible to obtain oxygen concentration detection output characteristics with good linearity which are proportional to oxygen concentration in the measured gas in a wide lean and rich region by regulating the diffused resistance, whereby it normally is not required to correct oxygen concentration detection output, thereby making A/F ratio control easy and improving accuracy of the A/F ratio control. Further, the oxygen concentration can be detected in either the first or second gas residence chamber depending on engine operating conditions to maximize either the speed of response or the accuracy of the detection.

Still further, it is possible to use the cells in the two gas residence chambers to compare signals produced with each other and assumed standards to develop corrections for those signals to compensate for abnormalities that occur abruptly or over a long period of use.

We claim:

1. A device for measuring a component of an engine exhaust gas to be analyzed, comprising,
    means forming a first chamber and a first diffusion restricting means for communicating the first chamber with the gas to be analyzed,
    a first electrochemical cell means having two electrodes and an oxygen ion conductive solid electrolyte therebetween with one electrode in said first chamber and the other electrode in communication with a gas outside the first chamber,
    means forming a second chamber and a second diffusion restricting means for communicating the second chamber with the gas to be analyzed at a different rate of diffusion than caused by said first diffusion restricting means,
    a second electrochemical cell means having two electrodes and an oxygen ion conductive solid electrolyte therebetween with one electrode in said second chamber and the other electrode in communication with a gas outside the second chamber,
    electrical circuit means connected to each of the electrodes of said first and second electrochemical cell means,
    engine operation condition detecting means for detecting an operation condition of the engine,
    said electrical circuit means including selector circuit means for selectively connecting one of said first and second electrochemical cell means to said electrical circuit means for selectively applying an imposed electrical signal from said electrical circuit means separately to either said first or second electrochemical cell means depending on said detected engine operating condition, and
    said electrical circuit means separately measuring a resultant electrical signal for each of said first and 2. The device of claim 1 wherein said means for selectively applying an imposed electrical signal include means for determining a characteristic of the gas to be analyzed and selecting the polarity of the imposed electrical signal applied based on said characteristic.

3. The device of claim 2 wherein the applied imposed electrical signal is a constant voltage.

4. The device of claim 2 wherein said means for determining a characteristic of the gas to be analyzed comprises an electrochemical cell.

5. The device of claim 2 wherein said means for determining a characteristic of the gas to be analyzed includes means for selectively disconnecting the imposed electrical signal from said first and second electrochemical cell means and separately measuring the voltage produced by said first and second electrochemical cell means.

6. The device of claim 5 wherein said polarity of the imposed electrical signal is selected on the basis of the measured voltage being above or below a predetermined magnitude.

7. The device of claim 5 wherein said other electrode of each electrochemical cell means communicates with a gas outside the first and second chambers that is different from the gas to be analyzed.

8. The device of claim 3 wherein said resultant electrical signal is an electrical current.

9. The device of claim 1 wherein said imposed electrical signal is an electrical voltage and said resultant electrical signal is an electrical current of variable amperage.

10. The device of claim 1 wherein said imposed electrical signal is an electrical current of a constant amperage and said resultant electrical signal is a variable electrical voltage.

11. The device of claim 1 wherein a third electrochemical cell means is provided and has two electrodes with one electrode in said first chamber and the other electrode in communication with a reference gas outside the first chamber, and means for measuring the voltage produced across the third electrochemical cell means.

12. The device of claim 11 wherein the polarity of the imposed electrical signal applied across said first electrochemical cell means is selected on the basis of the voltage measured by said third electrochemical cell means.

13. The device of claim 11 wherein a fourth electrochemical cell means is provided and has two electrodes with one electrode in said second chamber and the other electrode in communication with a reference gas outside the first chamber, and means for measuring the voltage produced across the fourth electrochemical cell means.

14. The device of claim 13 wherein the polarity of the imposed electrical signal applied across said second electrochemical cell means is selected on the basis of the voltage measured by said fourth electrochemical cell means.

15. The device of claim 1 wherein the gas to be analyzed is the exhaust gas in an exhaust pipe means of an internal combustion engine, and the device is connected to said exhaust pipe means with said first and second chambers in communication with the exhaust gas through said first and second diffusion restricting means.

16. The device of claims 1 or 15 wherein the communication of the gas to be analyzed to the second chamber is in series with the first chamber with said second diffusion restricting means in communication with said first chamber and said first diffusion restricting means in direct communication with the gas to be analyzed.

17. The device of claims 1 or 15 wherein the communication of the gas to be analyzed is in parallel to said first and second chambers with said first and second diffusion restricting means in separate direct communication with the gas to be analyzed.

18. The device of claims 1 or 15 wherein a third chamber is provided and has a third diffusion restricting means for communicating the third chamber directly with the gas to be analyzed, and said first and second chambers are in communication with said third chamber through said first and second diffusion restricting means, respectively.

19. The device of claims 1 or 15 wherein said first and second diffusion restricting means comprise first and second holes in a wall of the first and second chambers, respectively, and said first and second holes have a first and second length and a first and second diameter, respectively, for causing gas diffusion through each hole at first and second rates which are different.

20. The device of claims 1 or 15 wherein said first and second diffusion restricting means comprise first and second holes in a wall of the first and second chambers, respectively, and a porous filter means positioned in at least one of said holes for causing gas diffusion therethrough at a predetermined rate different from the gas diffusion rate through the other hole.

21. The device of claims 1 or 15 wherein a porous filter means comprises each said diffusion restricting means.

22. The device of claims 1, 9 or 10 wherein means are provided for comparing at least one of the two resultant electrical signal values to predetermined electrical signal values for determining the magnitude of the component in the gas to be analyzed.

23. The device of claims 1, 9 or 10 wherein means are provided for comparing the two resultant electrical signal values to predetermined electrical signal values for determining the magnitude of the component in the gas to be analyzed, and means for periodically comparing said two thusly determined magnitudes of the component for any difference therein and correcting the magnitude thereafter determined by and based on one of said resultant electrical signal values to correct any error represented by said difference.

24. The device of claim 23 wherein means are provided for causing said periodic comparing of said two thusly determined magnitudes during a substantially steady state condition wherein the amount of the component in the gas to be analyzed is relatively constant.

25. The device of claim 23 wherein said rate of diffusion is greater for said first chamber than said second chamber and the corrected magnitude of the component is made with respect to the resultant electrical signal value from said first electrochemical cell means.

26. The device of claim 1 for use in determining the air-fuel ratio during operation of an internal combustion engine having an exhaust pipe means wherein the gas to be analyzed is the exhaust gas in the engine exhaust pipe means and the component being measured is related to the air-fuel ratio, and said diffusion restricting means are in communication with said exhaust pipe means for conducting exhaust gas to said chamber.

27. The device of claim 26 wherein means are provided for causing the resultant electrical signal value from the first electrochemical cell means to be employed for determining the air-fuel ratio during transitions in the operation of the engine and the resultant electrical signal value from the second electrochemical cell means to be employed for determining the air-fuel ratio during steady-state operation of the engine.

28. The device of claim 27 wherein the said rate of diffusion is greater for said first chamber than said second chamber for causing faster responses by the electrochemical cell means therein to changes in the air-fuel ratio during said transitions in the operation of the engine and more accurate responses to changes in the air-fuel ratio during said steady-state operation of the engine than the corresponding responses by the cell means in the second chamber.

29. The device of claim 26 wherein the resultant electrical signal is electrical current and is at zero amperage at a predetermined air-fuel ratio.

30. The device of claim 29 wherein the polarity of the resultant electrical signal above and below said predetermined air-fuel ratio is reversed.

31. The device of claim 30 wherein an initial ratio of the resultant current electrical signal value to the air-fuel ratio for each said electrochemical cell means changes abruptly at the point of zero electrical current, and said initial ratio for the first electrochemical cell means above said predetermined air-fuel ratio is substantially the same as the initial ratio for the second electrochemical cell means below said predetermined air-fuel ratio.

32. The device of claim 31 wherein means are provided for determining the air-fuel ratio from said resultant electrical signal in said first electrochemical cell means at ratios above said predetermined air-fuel ratio and from said resultant current in said second electrochemical cell means at ratios below said predetermined air-fuel ratio for producing a substantially linear initial ratio at all air-fuel ratios.

33. The device of claim 26 wherein means are provided for selecting the second electrochemical cell means for measuring the resultant electrical signal when electrical current in the first electrochemical cell would be above a predetermined high level for the same air-fuel ratio.

34. The device of claim 30 wherein the resultant electrical signal is an electrical current and a graph of the values of the resultant electrical signal versus the air-fuel ratio for said first and second electrochemical cell means produces separate lines that have a slope that changes abruptly at the point of zero electrical current, and the slope of the line for the first electrochemical cell means for air-fuel ratios above said point is substantially the same as the slope of the line for the second electrochemical cell means for air-fuel ratios below said point.

35. A device for measuring a component of an engine exhaust gas to be analyzed, comprising,
   means forming first and second chambers,
   a first electrochemical cell means having first and second electrodes and an oxygen ion conductive solid electrolyte therebetween with the first electrode in said first chamber and the second electrode in communication with a gas outside the first chamber,
   a second electrochemical cell means having first and second electrodes and an oxygen ion conductive solid electrolyte therebetween with the first electrode in said second chamber and the second electrode in communication with a gas outside the second chamber, diffusion restricting means for causing communication of said gas to be analyzed with said first electrodes of said first and second electrochemical cell means at said different gas diffusion rates, electrical circuit means connected to each of the electrodes of said first and second electrochemical cell means, means for detecting an operating condition of the engine, said electrical circuit means including selector circuit means for selectively connecting one of said first and second electrochemical cell means to said electrical circuit means for selectively applying an imposed electrical signal from said electrical circuit means separately to either said first or second electrochemical cell means depending on said detected engine operating condition and said electrical circuit means separately measuring a resultant electrical signal for each of said first and second cell means for producing two values related to the proportion of the component being measured in the gas to be analyzed and for producing a measurement of said component from those two resultant electrical signals.

36. The device of claim 35 wherein the imposed electrical signal is an electrical voltage and the resultant electrical signal is current.

37. The device of claim 35 wherein the imposed electrical signal is electrical current and the resultant electrical signal is voltage.

38. A device for measuring a component of an engine exhaust gas to be analyzed, comprising, means forming a first chamber and a first diffusion restricting means for communicating the first chamber with the gas to be analyzed, said first chamber having a wall comprised of an oxygen ion conductive solid electrolyte with a first electrode mounted on said wall outside the first chamber, means forming a second chamber and a second diffusion restricting means for communicating the second chamber with the gas to be analyzed at a different rate of diffusion than caused by said first diffusion restricting means, said second chamber having a wall comprised of an oxygen ion conductive solid electrolyte with a third electrode mounted on said wall in said second chamber and a fourth electrode mounted on said wall outside the second chamber, electrical circuit means connected to the electrodes, means for detecting an operating condition of the engine, said electrical circuit means including selector circuit means for selectively connecting either said first and second electrodes or said third and fourth electrodes to said electrical circuit means for selectively applying an imposed electrical quantity from said electrical circuit means on said first and second electrodes and separately on said third and fourth electrodes mounted on said walls of said first and second chambers, respectively, in a quantity dependent on said detected engine operating condition, and said electrical circuit means separately measuring a resultant electrical quantity for producing two values of the component being measured in the gas to be analyzed and for producing a measurement of said component from those two electrical signals of those two values.

39. The device of claim 38 wherein the imposed electrical quantity is an electrical voltage and the resultant electrical quantity is an electrical current.

40. The device of claim 38 wherein the imposed electrical quantity is an electrical current and the resultant electrical quantity is an electrical voltage.

41. A device for measuring a component of an engine exhaust gas to be analyzed, comprising, means forming first and second chambers, a first electrochemical cell means having first and second electrodes and an oxygen ion conductive solid electrolyte therebetween with the first electrode in said first chamber and the second electrode in communication with a gas outside the first chamber, a second electrochemical cell means having first and second electrodes and an oxygen ion conductive solid electrolyte therebetween with the first electrode in said second chamber and the second electrode in communication with a gas outside the second chamber, diffusion restricting means for causing communication of said gas to be analyzed with said first electrodes of said first and second electrochemical cell means at different rates, means for detecting an operating condition of the engine, electrical circuit means connected to said electrodes of said electrochemical cell means and including selector circuit means for selectively connecting the first and second electrodes of either said first or second electrochemical cell means to said electrical circuit means for selectively applying an electrical signal across either said first or second electrochemical cell means with said signal dependent on the detected engine operating condition, and said electrical circuit means separately measuring a resultant electrical signal for producing two values proportional to the component being measure of the gas to be analyzed, and said electrical circuit means including means for comparing said two values with reference values for determining any abnormalities in the two values and correcting for any such abnormalities and for producing a corrected measurement of said gas component from those two values.

42. The device of claim 41 wherein means are provided for determining a substantially steady-state of the components of the gas to be analyzed for initiating the operation of said means for comparing said two values.

43. A device for measuring a component of an engine exhaust gas to be analyzed comprising a first sensor cell means having an oxygen ion conductive solid electrolyte for providing an output proportional to the concentration of the component in the gas to be analyzed; a second sensor cell means having an oxygen ion conductive solid electrolyte for providing an output substantially proportional to the concentration of the component in the gas to be analyzed and different in characteristics from the output of said first sensor means, electrical circuit means connected to said first and second sensor means, means for detecting an operating condition of the engine, said electrical circuit means including selector circuit means for selectively connecting said first or second sensor means for selectively applying an electrical signal to either said first or second sensor means which signal depends on the detected engine operating condition, a detection means for detecting abnormality of said first sensor means or said second sensor means according to a detecting value of component concentration from said first sensor means and a detection value of component concentration from said second sensor means, and means for producing a measurement of said component concentration from the two outputs of the first and second sensors.

44. The device of claim 43 wherein said first sensor means comprises a base forming first and second gas residence chambers each having oxygen ion conductive solid electrolyte wall portions, said first gas residence chamber being communicated through a first gas diffusion restricting means to the gas to be analyzed, said second gas residence chamber being communicated through a second gas diffusion restricting means to said first gas residence chamber, a first two pairs of electrodes provided on inside and outside surfaces of the electrolyte wall portions of said first gas residence chamber in such a manner that each electrode is arranged in opposed relation with respect to the electrolyte wall portions; said second sensor means comprises said base and a second two pairs of electrodes provided on inside and outside surfaces of the electrolyte wall portions of said second gas residence chamber in such a manner that each electrode is arranged in opposed relation with respect to the electrolyte wall portions.

45. A device for measuring a component of an engine exhaust gas to be analyzed, comprising, means forming a first chamber and a first diffusion restricting means for communicating the first chamber with the gas to be analyzed,
said first chamber having a wall means comprised of an oxygen ion conductive solid electrolyte and first and second pairs of electrodes with a first electrode of each pair mounted on said wall in said first chamber and a second electrode of each pair mounted on said wall outside the first chamber,
means forming a second chamber and a second diffusion restricting means for communicating the second chamber with the gas to be analyzed at a different rate of diffusion than caused by said first diffusion restricting means,
said second chamber having a wall means comprised of an oxygen ion conductive solid electrolyte and first and second pairs of electrodes with a first electrode of each pair mounted on said wall means in said second chamber and a second electrode of each pair mounted on said wall means outside the second chamber,
means for detecting an operating condition of the engine,
means for selectively measuring an electrical signal generated across each first pair of electrodes mounted on said wall means of each said chamber,
and means for selectively applying an electrical signal that is dependent on the detected engine operating condition across each second pair of electrodes mounted on said wall means of each said chamber and separately measuring a resultant electrical signal for producing two values proportional to the component of the gas being measured and for producing a measurement of the component from the two resultant electrical signals of the two values.

46. A device for measuring a component of a gas to be analyzed, comprising:
means forming a first chamber and a first diffusion restricting means for communicating the first chamber with the gas to be analyzed,
a first electrochemical cell means having two electrodes and a solid electrolyte therebetween with one electrode in said first chamber and the other electrode in communication with a gas outside the first chamber,
means forming a second chamber and a second diffusion restricting means for communicating the second chamber with the gas to be analyzed at a different rate of diffusion than caused by said first diffusion restricting means,
a second electrochemical cell means having two electrodes and a solid electrolyte therebetween with one electrode in said second chamber and the other electrode in communication with a gas outside the second chamber,
means forming a third chamber, a third diffusion restricting means for communicating the third chamber directly with the gas to be analyzed, said first and second chambers being in communication with said third chamber through said first and second diffusion restricting means, respectively, and
electrical circuit means connected to each of the electrodes of said first and second electrochemical cell means for selectively applying an imposed electrical signal separately to said first and second electrochemical cell means and for separately measuring a resultant electrical signal for each of said two cell means having a value related to the component being measured in the gas to be analyzed and for producing a measurement of said component from those two resultant electrical signals.

47. A device for measuring a component of a gas to be analyzed, comprising,
means forming a first chamber and a first diffusion restricting means for communicating the first chamber with the gas to be analyzed,
a first electrochemical cell means having two electrodes and a solid electrolyte therebetween with one electrode in said first chamber and the other electrode in communication with a gas outside the first chamber,
means forming a second chamber and a second diffusion restricting means for communicating the second chamber with the gas to be analyzed at a different rate of diffusion than caused by said first diffusion restricting means,
a second electrochemical cell means having two electrodes and a solid electrolyte therebetween with one electrode in said second chamber and the other electrode in communication with a gas outside the second chamber,
said first and second diffusion restricting means comprising first and second holes in a wall of the first and second chambers, respectively, and a porous filter means positioned in at least one of said holes for causing gas diffusion therethrough at a predetermined rate different from the gas diffusion rate through the other hole, and
electrical circuit means connected to each of the electrodes of said first and second electrochemical cell means for selectively applying an imposed electrical signal separately to said first and second electrochemical cell means and for separately measuring a resultant electrical signal for each said two cell means having a value related to the component being measured in the gas to be analyzed and for producing a measurement of said component from those two resultant electrical signals.

48. A device for measuring a component of a gas to be analyzed, comprising:
   means forming a first chamber and a first diffusion restricting means for communicating the first chamber with the gas to be analyzed,
   a first electrochemical cell means having two electrodes and a solid electrolyte therebetween with one electrode in said first chamber and the other electrode in communication with a gas outside the first chamber,
   means forming a second chamber and a second diffusion restricting means for communicating the second chamber with the gas to be analyzed at a different rate of diffusion than caused by said first diffusion restricting means,
   a second electrochemical cell means having two electrodes and a solid electrolyte therebetween with one electrode in said second chamber and they other electrode in communication with a gas outside the second chamber,
   said first and second diffusion restricting means each being comprised of a porous filter means, and
   electrical circuit means connected to each of the electrodes of said first and second electrochemical cell means for selectively applying an imposed electrical signal separately to said first and second electrochemical cell means and for separately measuring a resultant electrical signal for each said two cell means having a value related to the component being measured in the gas to be analyzed and for producing a measurement of said component from those two resultant electrical signals.

* * * * *